United States Patent
Bedi et al.

(10) Patent No.: US 11,624,748 B2
(45) Date of Patent: Apr. 11, 2023

(54) METHODS AND COMPOSITIONS FOR THE IDENTIFICATION OF EPITHELIAL TO MESENCHYMAL BREAST CANCER

(71) Applicant: Tuskegee University, Tuskegee, AL (US)

(72) Inventors: Deepa Bedi, Tuskegee, AL (US); Kelvin Jones, Tuskegee, AL (US)

(73) Assignee: TUSKEGEE UNIVERSITY, Tuskegee, AL (US)

( * ) Notice: Subject to any disclaimer, the term of this patent is extended or adjusted under 35 U.S.C. 154(b) by 307 days.

(21) Appl. No.: 17/125,657

(22) Filed: Dec. 17, 2020

(65) Prior Publication Data

US 2021/0263033 A1 Aug. 26, 2021

Related U.S. Application Data

(60) Provisional application No. 62/949,131, filed on Dec. 17, 2019.

(51) Int. Cl.
   *G01N 33/574* (2006.01)
   *A61K 49/00* (2006.01)
   *C07K 7/06* (2006.01)

(52) U.S. Cl.
   CPC ... *G01N 33/57415* (2013.01); *A61K 49/0002* (2013.01); *C07K 7/06* (2013.01)

(58) Field of Classification Search
   CPC . G01N 33/57415; A61K 49/0002; C07K 7/06
   See application file for complete search history.

(56) References Cited

U.S. PATENT DOCUMENTS

| 4,584,268 A | * | 4/1986 | Ceriani | G01N 33/57415 |
| | | | | 530/389.7 |
| 2003/0133927 A1 | * | 7/2003 | DeFeo-Jones | A61K 47/62 |
| | | | | 424/94.63 |
| 2016/0109450 A1 | * | 4/2016 | Lee | G01N 33/5011 |
| | | | | 435/7.1 |

* cited by examiner

*Primary Examiner* — Marcela M Cordero Garcia
(74) *Attorney, Agent, or Firm* — Terry M. Sanks, Esq.; Beusse Sanks, PLLC

(57) ABSTRACT

There is disclosed a method for selectively detecting epithelial to mesenchymal transition (EMT) phenotypic cells but not noncancerous/normal epithelial cells and breast fibroblasts in a biological sample or a patient. The compositions comprise novel binding peptides that specifically bind to EMT cancer cells. EMT phenotypic cells can be identified using the specific peptides and quantitatively measured by detection of a complex of the peptide and a detectable marker. Further, nanodevices incorporating specific EMT phage ligand may be used to identify EMT cancer cells in vivo. Also disclosed are the novel binding phage peptides, and compositions and nanodevices containing the phage ligand for carrying out methods of the invention.

6 Claims, 24 Drawing Sheets
(11 of 24 Drawing Sheet(s) Filed in Color)
Specification includes a Sequence Listing.

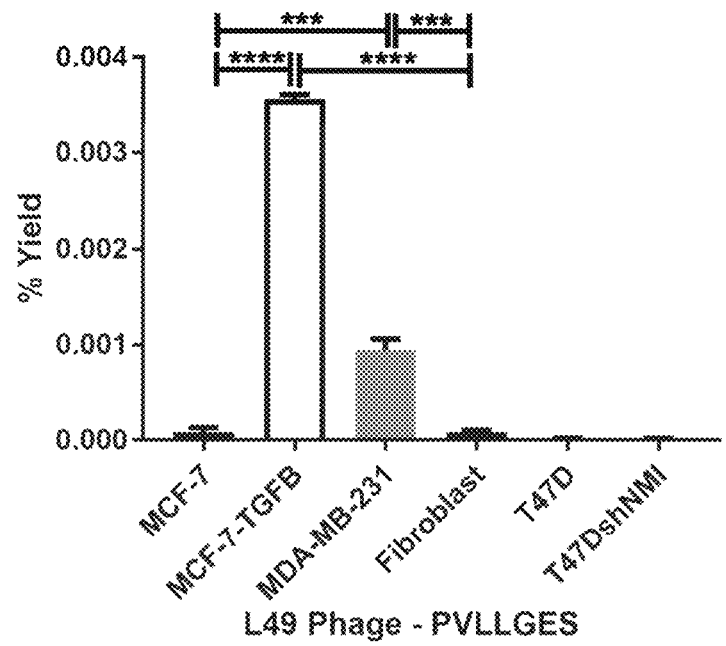

E9 Phage - ILNCMRN

E11 Phage - LGLRGSL

E12 Phage - ARKTNPL

E16 Phage - FNGPHTR

E20 Phage - TKFHFSG

E25 Phage - DFLTARL

Breast Fibroblast cells

MCF-7 cells

MCF-7TGFbeta cells

MDAMB231 cells

Normal Breast tissue

FIG. 8                                  Table I

| Eluate Phage Peptide Sequences | | | | | | |
|---|---|---|---|---|---|---|
| E9  | I | L | N | C | M | R | N |
| E11 | L | G | L | R | G | S | L |
| E12 | A | R | K | T | N | P | L |
| E16 | F | N | G | P | H | T | R |
| E20 | T | K | F | H | F | S | G |
| E25 | D | F | L | T | A | R | L |
| E29 | N | T | F | S | W | H | T |
| E32 | G | T | F | L | F | S |   |
| E42 | N | T | L | R | T | P | Y |
| E43 | H | H | D | N | V | A | M |
| E45 | P | N | L | P | W | V | P |
| E46 | Y | E | H | H | P | R | I |
| E48 | H | M | R | Q | G | M | A |

| Lysate Phage Peptide Sequences | | | | | | |
|---|---|---|---|---|---|---|
| L5  | T | H | S | S | W | G | M |
| L9  | N | M | W | E | S | V | P |
| L10 | R | E | G | H | M | G | V |
| L24 | K | D | S | H | E | P | W |
| L27 | T | L | A | T | G | G | M |
| L30 | P | Y | E | P | R | A | T |
| L42 | K | G | D | Y | K | L | F |
| L45 | S | I | L | S | K | N | H |
| L46 | E | R | S | G | M | H | S |
| L47 | H | W | P | A | K | H | I |
| L49 | P | V | L | L | G | E | S |

FIG. 9A

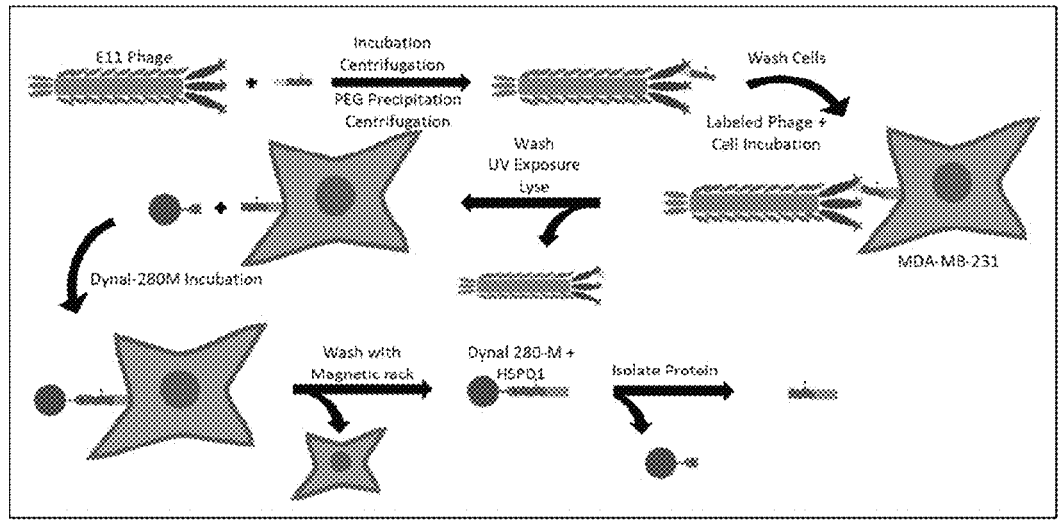

FIG. 9B

Fig. 9C

60kDa Heat shock protein, mitochondrial n=2 Tax=Homo sapiens RepID = CH60_HUMAN
5 exclusive unique peptides, 5 exclusive unique spectra, 8 total spectra, 48/573 amino acids (8% coverage)

```
MLRLPTVFRQ  MRPVSRVLAP  HLTRAYAKDV  KFGADARALM  LQGVDLLADA  VAVTMGPKGR
TVIIEQSWGS  PKVTKDGVTV  AKSIDLKDKY  KNIGAKLVQD  VANNTNEEAG  DGTTTATVLA
RSIAKEGFEK  ISKGANPVEI  RRGVMLAVDA  VIAELKKQSK  PVTTPEEIAQ  VATISANGDK
EIGNIISDAM  KKVGRKGVIT  VKDGKTLNDE  LEIIEGMKFD  RGYISPYFIN  TSKGQKCEFQ
DAYVLLSEKK  ISSIQSIVPA  LEIANAHRKP  LVIIAEDVDG  EALSTLVLNR  LKVGLQVVAV
KAPGFGDNRK  NQLKDMAIAT  GGAVFGEEGL  TLNLEDVQPH  DLGKVGEVIV  TKDDAMLLKG
KGDKAQIEKR  IQEIIEQLDV  TTSEYEKEKL  NERLAKLSDG  VAVLKVGGTS  DVEVNEKKDR
VTDALNATRA  AVEEGIVLGG  GCALLRCIPA  LDSLTPANED  QKIGIELIKR  TLKIPAMTIA
KNAGVEGSLI  VERIMQSSSE  VGYDAMAGDF  VNMVEKGIID  PTKVVRTALL  DAAGVASLLT
TAEVVVTEIP  KEEKDPGMGA  MGGMGGGMGG  GMF
```

METHODS AND COMPOSITIONS FOR THE IDENTIFICATION OF EPITHELIAL TO MESENCHYMAL BREAST CANCER

RELATED APPLICATIONS

This application claims priority to U.S. provisional application 62/949,131 filed on Dec. 17, 2019, which application is incorporated by reference in its entirety.

This invention was made with government support under grant numbers SC2CA11028-01 and G12 RR03059-21A1, awarded by the National Institutes of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on Feb. 26, 2021, is named 057193-000039_SL.txt and is 10,736 bytes in size.

FIELD OF THE INVENTION

The present invention relates to methods and compositions for the diagnosis of metastatic breast cancer. The methods and compositions can be used to determine whether a subject has or is at risk for developing metastatic breast cancer. The compositions of the invention can include novel binding peptides that specifically bind to epithelial to mesenchymal transition (EMT) phenotypic cells and not to normal epithelial cells or other mesenchymal cells such as fibroblasts. In particular, the compositions include novel binding phage peptides that are able to identify metastatic breast cancer cells. Further still, the peptide complex that includes a novel binding peptide can be used in cancer imaging techniques. Further the methods can include profiling breast cancer tumors for optimization of therapeutic treatment regimens. The binding peptides can also be used in cancer therapeutic treatments as a vehicle to target and deliver cancer therapeutics to breast cancer cells where the therapeutic has been complexed to the binding peptides.

BACKGROUND

Mortality from breast cancer has steadily been declining over the past decade, due to earlier detection, adjuvant therapies and the advent of targeted therapies for estrogen receptor-positive and HER2-positive cancers. Despite advances in diagnosis and treatment, however, breast cancer remains an important cause of both morbidity and mortality. Indeed, breast cancer is the most common cancer in women and the second leading causes of death due to cancer. [1] The cause of death in breast cancer patients is often due to metastasis to distant sites, resulting in organ failure accounting for a 5-yr survival rate of 23%. Evidence supports the observation that metastasis is an early event in breast cancer progression, with possibly up to 90% of patients already having metastasis at the time of diagnosis. Studies have shown that dissemination of cancer cells and metastasis into distant organs is often preceded by an epithelial to mesenchymal transition (EMT) of cancer cells [3]. EMT is a process by which the epithelial cells dedifferentiate to acquire mesenchymal phenotype. This process involves an increase in fibroid morphology, enhanced migratory and invasive properties, resistance to apoptosis and an increase in extracellular matrix components, enabling the cells to invade through the stroma and migrate and seed to distant organs [4, 5]. EMT concludes with the acquisition of cell motility and invasiveness by the reorganization of the cytoskeleton dynamics such as the rearrangements of the intercellular junctions and the changes in apical-basal polarity, meaning the acquisition of EMT in the epithelium of an organ enables the path to tumorigenesis. EMT has more recently been linked to the progression of cancer. An increase in EMT markers has been linked with aggressiveness of metastatic disease, which may be explained partially by intrinsic resistance to standard therapies. The concept of EMT in breast cancer has been well demonstrated in numerous in vitro studies in different normal, malignant mammary epithelial cells and in mouse models of mammary cancers [6, 7]. It has been suggested that tumor microenvironment [8] and growth factors, including but not limited to, transforming growth factor beta (TGFβ), epidermal growth factor (EGF), platelet-derived growth factor (PDGF) has a dramatic effect on epithelial phenotype and in promoting motility and invasiveness via the induction of EMT [9; 10]. TGFβ treatment changes epithelial cells from cubodial shape to more elongated ones with concomitant loss of epithelial markers and increased expression of mesenchymal markers vimentin, fibronectin and α-smooth muscle actin [11]. These EMT markers are also present in activated cancer-associated fibroblasts (CAFs), which contributes to the pathogenesis of tumor progression and invasiveness [12]. Several studies support a physiologic role of EMT during tumor progression [13; 14; 15] by monitoring EMT progression by the cadherin switch, E-cadherin to N-cadherin, which is normally also present in mesenchymal cells, fibroblasts, neural tissue [16]. Similarly, vimentin, a type III intermediate filament (IF) protein that is expressed in mesenchymal cells, is also often used to define cancer cells undergoing EMT; vimentin, however, is also present in fibroblasts, endothelial cells, cells of the hematopoietic lineages, and glial cells [17; 18]. Therefore, there is a need for specific ligands that can recognize and define EMT in tumor and in cancer-associated fibroblasts.

Current detection methods, such as imaging techniques including computed tomography (CT) scans, magnetic resonance imaging (MRI), positron emission tomography (PTE) and angiography, can be unreliable due to low sensitivity and the potential for operator error. Imaging techniques currently may be less accurate for the detection of EMT, as well, in smaller, early stage tumors. There is a continuing need for new and enhanced methods of diagnosing and treating metastatic breast cancer. Further, there is a need for ligands that can be used to identify EMT status and metastatic cells in tumor tissue samples as well as for use as an improved in vivo imaging diagnostics. The present invention meets this need.

SUMMARY OF THE INVENTION

The invention provides peptides, such as LGLRGSL (SEQ ID NO: 1), which bind specifically to EMT breast cancer cells and do not bind to normal epithelial cells and breast fibroblasts. The invention provides peptide complexes, which comprise a peptide of the invention, such as LGLRGSL (SEQ ID NO: 1), bound to a marker for detection or bound to a therapeutic drug or compound used to treat/kill cancer cells.

The peptides can be used as probes for molecular imaging. Peptide complexes provided herein can be used in in vivo applying known imaging techniques. The peptides can be used to profile cancer tumor for optimization of therapeutic treatment schemes.

The peptides can be used to identify and isolate cancer-specific receptors as potential components for development of therapeutic antibodies, anticancer vaccines and diagnostics. The peptides can be used in diagnostic methods, particularly as a method to diagnosis the presence of EMT breast cancer cells in a mammal because the peptides of the invention do not attach to normal healthy breast tissue or epithelial cells and normal fibroblasts.

Nucleic acids encoding the peptide are also embodiments of the invention.

Peptides provided herein can be used in diagnostic methods, especially as a method to diagnosis the presence of EMT breast cancer cells (such as but not limited to HCC and ICC) in a mammal since the peptide binds to EMT cells whereas it does bind to normal epithelial breast cancer cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A is E11 phage LGLRGSL (SEQ ID NO: 1). FIG. 3B is E12 phage ARKTNPL (SEQ ID NO: 2). FIG. 3C is E32 phage GTFLFS (SEQ ID NO: 3). FIG. 3D is E45 phage PNLPWVP (SEQ ID NO: 4). FIG. 3E is E46 phage YEHHPRI (SEQ ID NO: 5). FIG. 3F is E48 phage HMRQGMA (SEQ ID NO: 6). FIG. 3G is L24 phage KDSHEPW (SEQ ID NO: 7). FIG. 3I is L49 phage PVLLGES (SEQ ID NO:11. All data represent the mean±S.D. $*p<0.05$, $p\leq0.01$, $*p\leq0.001$, $****p\leq0.0001$.

FIG. 4A is E9 phage ILNCMRN (SEQ ID NO: 10). FIG. 4B is E11 phage LGLRGSL (SEQ ID NO: 1). FIG. 4C is E12 phage ARKTNPL (SEQ ID NO: 2). FIG. 4D is e16 phage FNGPHTR (SEQ ID NO: 11). FIG. 4E is E20 phage TKFHFSG (SEQ ID NO: 12). FIG. 4F is E25 phage DFLTARL (SEQ ID NO: 13). FIG. 4G is E29 phage NTFSWHT (SEQ ID NO: 14). All data represent the mean±S.D. $*p<0.05$, $p\leq0.01$, $*p\leq0.001$, $****p\leq0.0001$.

FIG. 6 A-6D depicts the phage LGLRGSL (SEQ ID NO: 1) (E11) stained selective to EMT phenotypic cells in Immunofluorescence microscopy analysis.

FIG. 7A shows invasive carcinoma T3N0M0. The blue arrow denotes phage binding to cancer cells while red arrowhead shows stroma. FIG. 7B shows invasive carcinoma T3N1aM0. FIG. 7C shows invasive carcinoma T2N0M0. FIG. 7D shows metastasis in lymph nodes. FIG. 7E shows no staining was observed in normal breast tissue.

FIG. 8 (Table 1) shows phage peptide sequences from isolated eluate and lysate phages from third round of selection against MCF/TGFβ breast cancer cells. FIG. 8 discloses SEQ ID NOS 10, 1, 2, 11-14, 3, 16-17, 4-6, 18-20, 7, 21-22, 8, 23-25 and 9, respectively, in order of columns.

FIG. 9A shows a schematic depiction of an experiment where the E11 phage is labeled with a biotin tag. The biotinylated phage immobilizes the receptor protein. The Dynal magnetic beads are then functionalized with streptavidin. FIG. 9B shows protein expression of HSPD1 isolated from MDA-MB-231—Pulldown run on SDS-page gel. To visualize the protein, the SDS-page gel was treated with silver nitrate staining. FIG. 9B discloses SEQ ID NO: 26. FIG. 9 C provides the sequence of Heat shock protein (HSPD1), mitochondrial n=2 Tax=*Homo sapiens* RepID=CH60_HUMAN 5 exclusive unique peptides, 5 exclusive unique spectra, 8 total spectra, 48/573 amino acids (8% coverage). FIG. 9C discloses SEQ ID NO: 27.

FIG. 10B and FIG. 10C shows that protein expression of HSPD1 is high in MDA-MB-231 and MCF-7 overexpressing growth factor TGFβ. FIG. 10C shows from Immunofluorescence studies that there is increased binding for MDA-MB-231 when contrasted with 4T1.

FIG. 11A provides a schematic of a polyclonal inhibition plaque binding assay. FIG. 11B provides a bar graph that displays inhibition of E11 peptide phage to MDA-MB-231 $*p>0.05$ and to MDA-MB-468 $**p>0.01$.

FIG. 12A shows that patients have lower levels of HSPD1 tend to survive longer, whereas patients that have high levels of HSPD1 tend to die sooner. FIG. 12B shows that patients with Stage 1, 2, 3 or 4 cancer express more HSPD1 than patients not having cancer.

DETAILED DESCRIPTION

Figure 1:
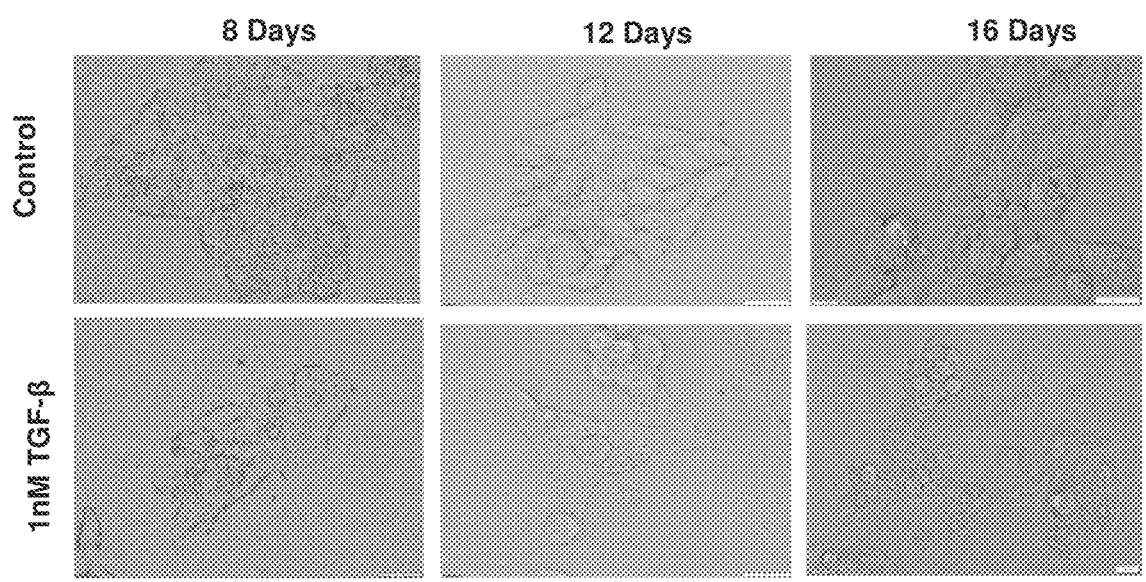
FIG. 1 depicts morphological changes in MCF-7 cells during TGFβ-induced EMT, in particular, images of cells treated long term (16 days) with TGFβ showing morphological changes as compared with control.

The present invention is based, in part, on the discovery that binding phage peptides can identify EMT in breast cancer. More specifically, the inventors have found that binding phage peptide having the amino acid sequence of LGLRGSL (SEQ ID NO: 1) is specific to receptors located on EMT cells but not normal breast tissues or normal fibroblasts. This peptide can serve as a novel probe for metastatic breast cancer diagnoses and imaging as well as in a complex where the peptide is coupled to a cancer therapeutic to allow delivery of the therapeutic to cancer cells. Also featured are methods of using the peptide complexes for the detection of a metastatic breast cancer and/or treatment of breast cancer.

Also provided are methods for identification of phages that specifically and selectively bind to mesenchymal breast cancer cells. Methods include the following steps:

A. Selection of phages from a phage library (the phage library contains peptides constructed at the N terminus of the minor coat protein (cpIII) of M13 phage) that specifically bind to mesenchymal breast cancer cells.
  A1. Select phages from phage library after depletion.
  A2. Incubate selected phages with MCF-7/TFGβ cells to allow binding of phages to the cells. Wash away unbound phages.
  A3. Elute cell associated phages and also recover cell internalized phages.
  A4. Amplify cell associated phages and cell internalized phages from step A3 and perform a second and third round of selection using the same protocol of depletion of the amplified phages against breast fibroblasts to obtain recovered phages after depletion.
  A5. Select at least one phage from step A4 and propagate and isolate and sequence DNA from the at least one phage.

B. Selecting phages that selectively bind target EMT cells, MCF-7/TFGβ, MDA-MB-231 or T47D-shNMI cells and not to breast fibroblasts or epithelial subtype breast cancer cells MCF-7 and T47D in a phage capture assay and/or phage based ELISA.
  B1. Perform phage capture assay or ELISA to identify phages that selectively bind target EMT cells, MCF-7/TFGβ, MDA-MB-231 or T47D-shNMI cells and not to breast fibroblasts or epithelial subtype breast cancer cells MCF-7 and T47D to obtain at least one positive phage.

C. Validating the at one positive phage obtained in step B1 for the ability to bind to EMT target cells in vitro using immunofluorescence analysis to further confirm specificity of phage peptide towards breast cancer cells with an EMT phenotype.

D. Validating phage peptide binding to human breast cancer ex vivo to identify at least one phage that specifically and selectively binds to mesenchymal breast cancer cells.

Peptide and Peptide Complex

The compositions provided herein include peptides that specifically bind to breast cancer cells with EMT phenotypic cells and that do not bind to normal fibroblasts.

LGLRGSL (SEQ ID NO: 1) is a small peptide that has been shown to selectively bind to EMT phenotypic cells. The LGLRGSL amino acid sequence is provided as SEQ ID NO. 1. The peptides of the present invention have advantages over fully length proteins or antibodies, including their small size, implying good tissue diffusion, target accessibility with no antigenicity, easy synthesis and adequate labeling and delivery, including but not limited to fluorescence labeling, radiolabeling or nanoparticle-targeted delivery. Further, the peptide complex may also include a contrast agent for improving the sensitivity and specificity of EMT phenotypic breast cells.

Table 1 (FIG. 8) provides additional peptide sequences of the present invention. E11, E32 and E45 are especially preferred since they are specific to (only bind) receptors located on EMT cells but not bind to normal breast tissues or normal fibroblasts.

A peptide of the present invention can be linked to a chelator that can bind radioactive metals to form a radio peptide complex that can be injected intravenously into the circulation of a subject with a potential metastatic tumor. The radio peptide complex of the present invention will be distributed throughout a subject's body and, if a patient has EMT phenotypic cells, it will selectively bind to these EMT phenotypic cells and may be actively taken up by the cancer cells. Thus, the radioactivity of the radio peptide complex will be amenable to detection through imaging techniques, including scanning and PET. The sensitivity of this imaging using the radio peptide complex of this invention will allow the identification of EMT phenotype breast cells in vivo. In a similar manner, labels could be used for additional imaging techniques. Detectable labels can include enzymes, photoaffinity ligands, radioisotopes, and fluorescent or chemiluminescent compounds. Alternatively or in addition, detectable labels include, but are not limited to, a radiopaque or contrast agent.

Molecular Target of the Peptides on EMT Breast Cancer Cells

Figure 10A:
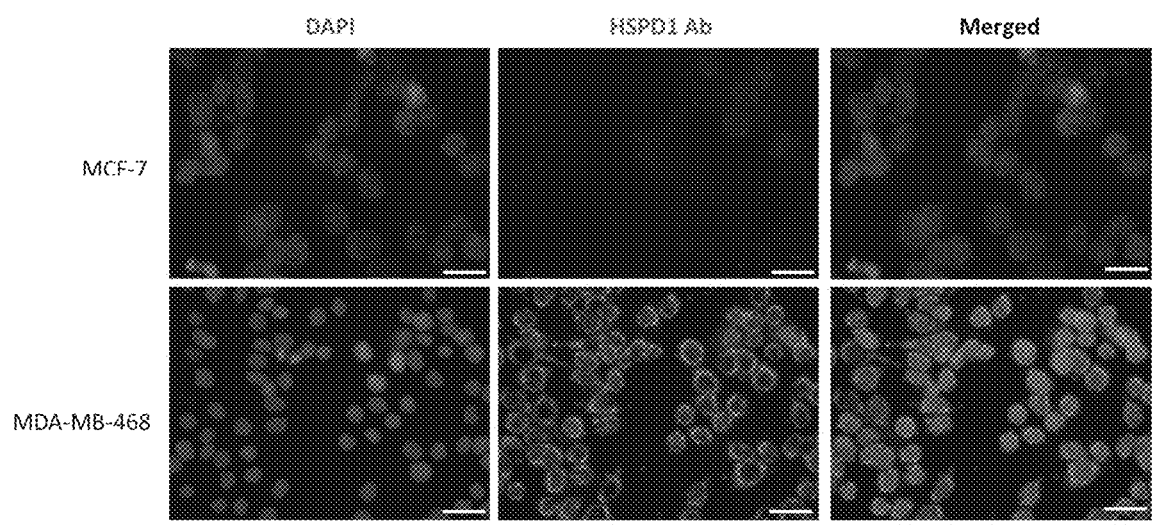
FIG. 10A shows the immunofluorescence staining of aggressive cancer cell line which displays HSPD1 expression and localization in cytoplasm. Cytoplasmic binding of HSPD1 polyclonal antibody (red) was determined by immunofluorescence. Images shown are representative of three individual experiments. Images were taken at 600 magnification. The measurement bar is 20 μm.
Figure 10B:
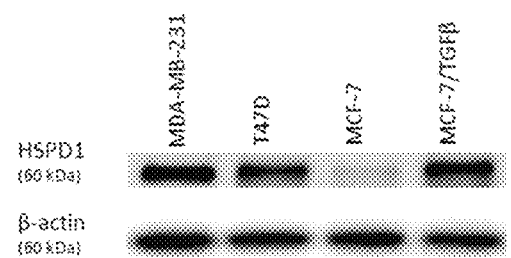
FIG. 10B shows that HSPD1 displays increased infinity for aggressive cancer cell lines.
Figure 10C:
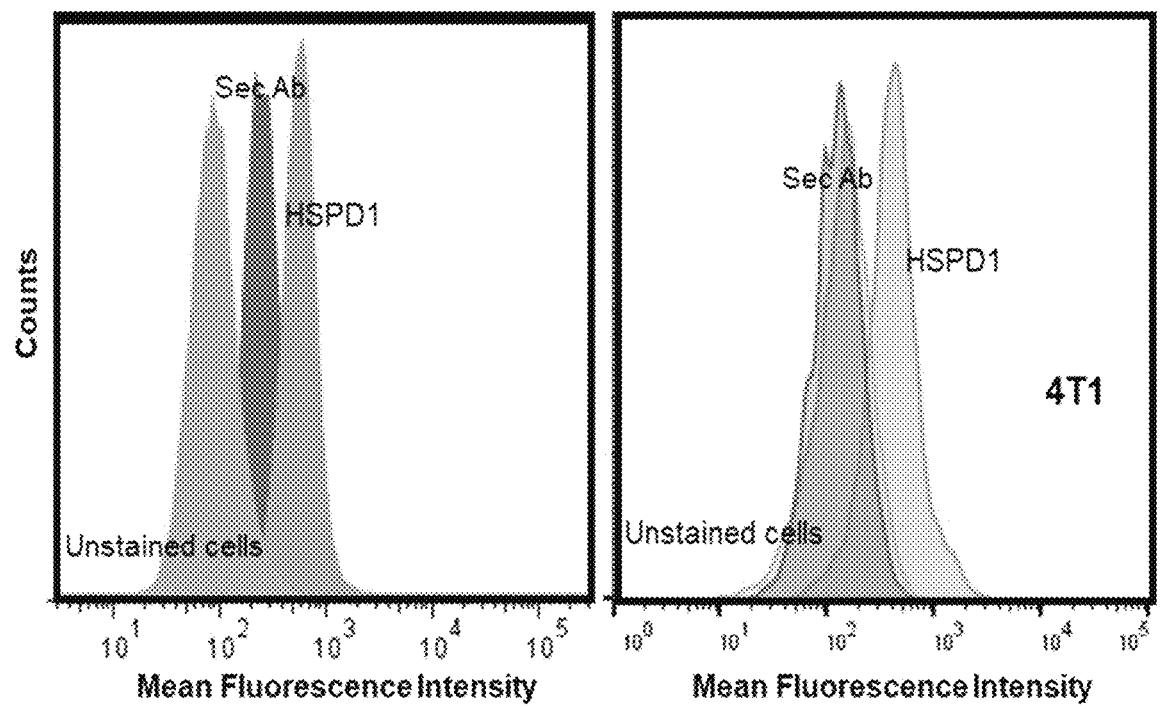
Figure 11A:
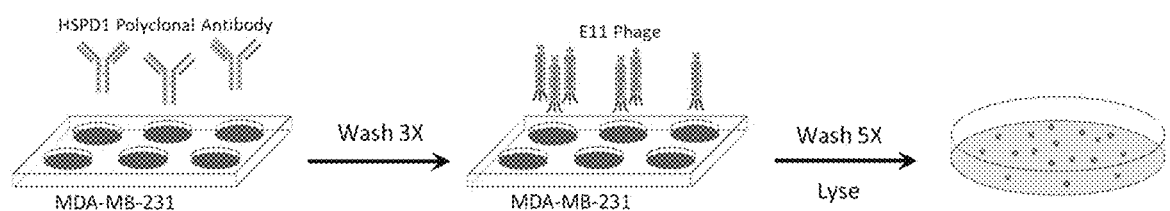
FIG. 11A-11B show that the HSPD1 polyclonal antibody inhibits binding of E11 peptide phage.
Figure 11B:
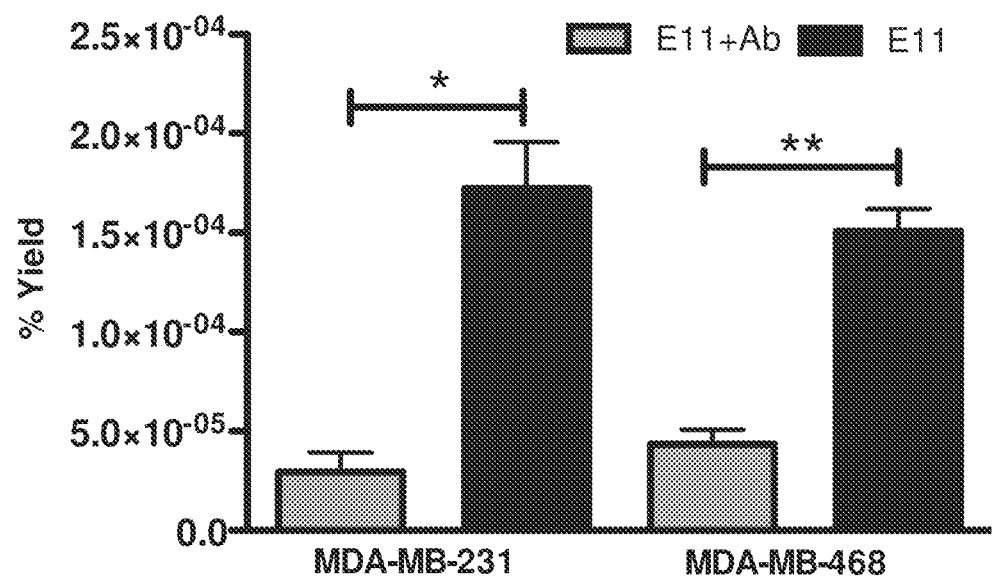
Figure 12:
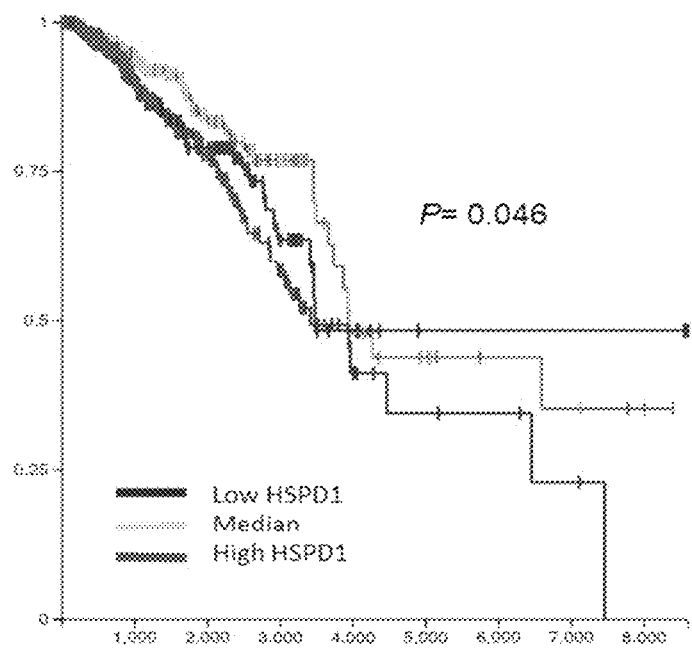
FIG. 12A and FIG. 12B shows that patients displaying high levels Hspd1 reveal a low survival rate, however, patients with low expression exhibit increased survival.
Figure 12B:
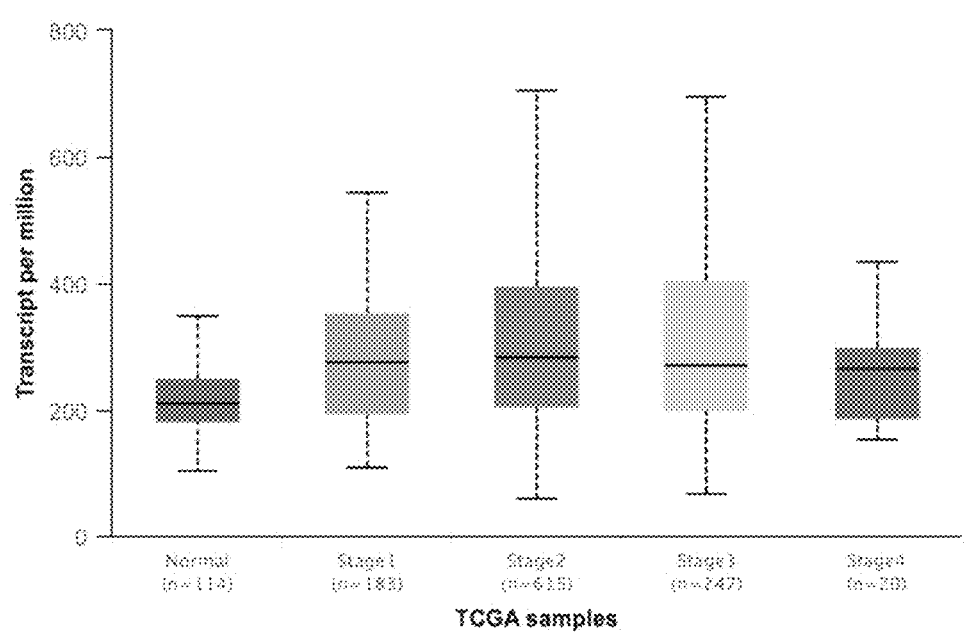

It has been determined that the E11 phage (the phage bearing the peptide LGLRGSL (SEQ ID NO: 1)) binds to heat shock protein HSPD1. The amino acid sequence of HSPD1 is provided in FIG. 9B. See FIG. 10A, which shows the presence of HSPD1 on MCF-7 and MDA-MB-468 cells. In addition, FIG. 10B and FIG. 10C shows that HSPD1 is highly expressed in MCF-7 and MDA-MB-231, which are both aggressive cancer cell lines.

The present invention also includes nucleic acids that encode the phage peptides of the invention.

The compositions disclosed herein are generally useful for the diagnosis of EMT phenotypic cells in breast cancer in a subject having a breast cancer or who is at risk for breast cancer. We may refer to a subject, patient, or individual interchangeably.

A biological sample or sample refers to a sample obtained or derived from a patient. The sample can be, for example, a body fluid sample, including blood, serum, plasma, urine, saliva, cerebral spinal fluid, mucus, and amniotic fluid. In some embodiments, a biological sample can be a tissue sample. Exemplary tissue samples include a biopsy specimen, such as a breast biopsy, a lymph node biopsy, or a primary cell culture prepared from a patient's cells, or supernatant from the primary culture.

The imaging techniques used for the in vivo detection of EMT phenotypic breast cancer cells in a subject can include fluorescence imaging, the use of nanoparticle based molecular beacons, or the use of radioactive imaging.

Methods disclosed herein are useful in the detection of EMT breast cancer in a patient suspected of having or at risk for EMT breast cancer. The methods can also be used in the analysis of samples from a patient who has been treated for breast cancer, in order to determine whether the patient is at risk for experiencing a metastatic breast cancer. The methods can also be used for monitoring the course of the treatment, to determine efficacy of the treatment and to allow the clinician to alter the treatment if needed. The methods may also be used in the detection, monitoring, or analysis of a patient suffering from or at risk of developing EMT breast cancer associated with the level of peptide such as LGLRGSL (SEQ ID NO: 1) in a biological sample, for example, a blood or serum sample, obtained from the patient.

The methods disclosed herein can be used either in conjunction with or as an enhancement of other standard diagnostic methods, for example serological analyses, ultrasound (sonography), computed tomography (CT scan), magnetic resonance imaging (MRI), angiography, laparoscopy, or biopsy.

EXAMPLES

Example 1: Identification of Phage Peptide Using Phage Display

Phage display offers considerable advantages as a high throughput profiling technology based on peptide libraries present on the surface of bacteriophage. Selective binding of phages from a library with billions of diversified peptides can make a clear distinction between two morphologically same, but functionally different, targets and thus, offers a complementary approach for comparative screening. Usually peptides can be displayed on the N-terminus of pIII protein coat protein (pIII phage display), which is displayed at one end of the filamentous phage in 3-5 copies [19] or can be displayed on the N-terminus of all copies of pVIII major coat protein [20]. Diversity of pIII or pVIII combinatorial phage library has been exploited extensively to explore the cell surface repertoire of various cancer cells such as, colon [21], prostate [22; 23], pancreatic [24], breast [25; 26] and to select many cell surface or cell internalizing peptides. Some of these highly specific and high affinity ligands have been used as diagnostic [24], molecular and targeting agents [27; 28; 29; 30]. Additionally, lamba (T7) phage display has been used to identify vascular zip codes [31] and markers for angiogenesis [32]. These studies and more define the power of using combinatorial phage display to identify molecular differences and interactive regions of the proteins without knowing the nature of interaction.

In this study, a novel method to use phage display libraries for identification of phages that can specifically and selectively bind to the mesenchymal breast cancer cells in vitro was developed. Since TGFβ is a known inducer of EMT, a model of TGFβ induced EMT in MCF-7 breast cancer cells was used (MCF-7/TGFβ) for selection of EMT-specific phages. The CX7C PhD phage library was used for selection of phages binding to MCF-7/TGFβ cells after subtractive depletion from breast fibroblasts. These selected phages were then tested on breast cancer cells that exhibited EMT phenotype (MDA-MB-231 and T47D-shNMI).

Materials

The PhD CX7C phage library was purchased from New England Biolabs (NEB). Fetal calf serum (FCS) and DMEM medium were purchased from Sigma (USA). The phage display library contains random peptides constructed at the N-terminus of the minor coat protein (cpIII) of M13 phage. The titer of the library is $2.3 \times 10^{13}$ pfu (plaque-forming units). The library contains a mixture of $3.1 \times 10^9$ individual clones, representing an entire obtainable repertoire of 7-mer peptide sequences, which expresses random 7-amino-acid sequences. The *Escherichia coli* host strain ER2738 (F+ strain, New England Biolabs) was used for M13 phage propagation. The human breast cancer cell lines MDAMB231, MCF-7 and breast fibroblasts (Hs 578T) were purchased from the American Type Culture Collection. MCF-7 cells were treated with 1 ng/mL of TGFβ for 16 days. MCF-7, and MDA-MB-231, MCF-7/TGFβ breast cancer cells were maintained in Dulbecco's modified Eagle's medium supplemented with 10% fetal bovine serum (Sigma) at 37° C. in an incubator containing 5% $CO_2$ and humidified air. Breast fibroblasts were maintained in special hybricare medium supplemented with 15% FBS (ATCC).

Methods/In Vitro Phage Selection

Biased protocol for selection of phages was employed as described [26] with some modifications. The PhD phage library (Cx7C) was depleted against a cell culture flask and breast fibroblasts (Hs 578T). Unbound phages recovered from the depletion were incubated with confluent MCF-7/TGFβ cells in a complete serum-containing media at room temperature for 1 h. Unbound phages were washed away and cell-associated phages were eluted with elution buffer (200 mM glycine-HCl, 1 mg/ml BSA, 0.1 mg/ml phenol red, pH 2.2) for 10 min on ice. The eluate was neutralized with 376 μl of 1M Tris (pH 9.1). Internalized phages were recovered with lysis buffer (2% CHAPS, 10 mM Tris, 2 mM EDTA (pH 8.0)) after further washing. The phage input and output were titered in bacteria as described previously [29]. The results were expressed as a percentage of a ratio of output to input phage. The eluted phage and cell-internalized phage were amplified separately in bacteria and used in the second and third round of selection using the same protocol of depletion of the amplified phages (lysate and eluate) against breast fibroblasts and incubating MCF-7/TGFβ cells with unbound phages recovered from depletion. 60 phages from the third round of selection were randomly picked and were propagated in the ER2738 bacteria. DNA was isolated form these 60 propagated clones using DNA isolation kit (QIAGEN GmbH, Hilden, Germany) and individual phage DNA sequences were identified. A primer used for sequencing was 5'-CCC TCA TAG TTA GCG TAA CG-3' (SEQ ID NO: 15) (−96 gIII sequencing primer, provided in the PhD-CX7C Phage display peptide library kit (NEB, MA).

Cell-Based ELISA and Phage Capture Assay

Individual phage clones were characterized for their selectivity toward EMT cells, MCF-7/TGFβ and MDA-MB-231 breast cancer cells in comparison with epithelial breast cancer cells, MCF-7, T47D, and breast fibroblasts using phage capture assay [29] and cell-based ELISA.

In phage capture assay, briefly, target cells MCF-7/TGFβ, MDA-MB-231, MCF-7, T47D, T47D-shNMI and breast fibroblasts were cultivated in triplicate to confluence in separate wells of 12-well cell culture plates. The medium with serum was incubated in separate wells in triplicate as a control. Cells were incubated with phage ($1 \times 10^{10}$ pfu) at RT for 1 h. Unbound phages were carefully removed and cells were washed with 100 μl washing buffer for 5 min eight times to remove non-specifically interacting phages. Cells were lysed with 500 lysis buffer (2.5% CHAPS) for 10 min on a rocker. The lysate containing cell-interacting phages was titered in *E. coli* ER2738 bacterial cells. Phage recovery was calculated as a ratio of output to input phage.

ELISA

Confluent monolayers of MCF-7/TGFβ, MDA-MB-231, MCF-7, T47D, T47D-shNMI and breast fibroblasts cells were incubated at room temperature with individual phage clones ($10^{10}$ PFU), for 1 hour at RT. Subsequently, cells were washed with PBS containing 0.1% Tween-20, incubated with primary anti-M13-biotin antibody (1:1000), for 1 h, at RT. Cells were washed again with PBS containing 0.1% Tween-20, incubated with secondary antibody streptavidin-HRP (1:2000, 45 min, RT), developed with tetra methyl benzidine and read at absorbance 650 with microplate reader (BioTek).

Example 2: Phage Capture Assay of Phage Binding to Cancer-Conditioned Media Activated Fibroblasts Breast fibroblasts were plated in a 12.5 cm flask cultured until approximately 70% confluent. Once properly confluent, fibroblasts were then cultured in MDA-MB-231 conditioned media or normal fibroblasts media for 72 hours. Thereafter, they were exposed to E11 phage ($10^8$ pfu) for 2 hours and analyzed for binding in phage capture assay as described above.

Example 3: Immunofluorescence Study of Selected Phages

MCF-7, MCF-7/TGFβ, MDA-MB-231 and Hs578T (breast fibroblasts) cells were seeded in a 4-well chamber overnight. On the next day, cells were fed with fresh medium. LGLRGSL (SEQ ID NO: 1) (E11) ($10^8$ pfu) was added in fresh medium and incubated at RT for one hour. After removing the unbound phages, cells were washed with wash buffer (0.1% tween-20 in PBS) three times and fixed with 4% formaldehyde for 15 minutes at 37° C. Cells were permeabilized with 0.2% Triton X-100 at RT for 10 minutes. Reagent was removed and cells were washed with TBS 3 times. Before incubation with anti-phage antibody, cells were treated with blocking buffer for 30 minutes at RT. Cells were incubated with M13-pIII monoclonal antibody for 1 hour at RT, washed and incubated with the secondary goat anti-mouse IgG antibody labeled with Alexa Flour® 488 (Molecular Probes) at a dilution of 1:500 in PBS containing 1% BSA for 45 minutes at RT. Cells were washed three times after secondary antibody treatment. TOTO-3 was used for nucleus staining. Cells were covered with cover slides with Prolong Gold Anti-fade Reagents. Nail polish was used to seal the slide. Pictures were taken by using the NIKON eclipse TE 2000-E confocal microscope.

Example 4: Phage Binding to Breast Cancer Tissue Microarrays

The breast tissue microarrays were obtained from Novus Biological (Littleton, Colo.). These include 40 breast cancer infiltrating ductal carcinoma, 10 metastatic lymph node and 9 adjacent normal breast tissues. The use of tissue was approved by the Institutional Review Board of Tuskegee University. Clinico-histopathologic characteristics of the subjects in the tissue microarray study included age, grade, hormone status and clinical stage, according to information provided by the suppliers. The expression levels were classified as negative (≤0.3), weak positive (0.3 to 1.5), or strong positive (≥1.5). Tissues were de-paraffinized in xylene and rehydrated in graded alcohols. For antigen retrieval the slides were pressure-cooked for 10 minutes. Endogenous peroxidase activity was quenched with 3% hydrogen peroxide for 5 minutes. vSlides were treated with LGLRGSL phage (SEQ ID NO: 1) ($10^{10}$ pfu) overnight. Slides were subsequently washed and blocked by 3% goat serum at room temperature for 1 hour in humidity chambers. Slides were then treated with M13-pIII phage monoclonal antibody (NEB, MA) or Vimentin antibody (Cell Siganling, Danvers, Mass.) (1:100). The HRP conjugated goat anti-mouse secondary antibody (Jackson Immunoresearch Laboratories Inc, West Grove, Pa.) was applied for 40 minutes. The antigen-antibody reaction was visualized after diaminobenzidine (Sigma-Aldrich, MO) was applied for 7 minutes. The slides were counterstained with hematoxylin (Sigma-Aldrich, MO) for 1 minute. Positive controls were included in each staining run; negative controls were obtained by omitting the primary antibody. Slides were then dehydrated in alcohols and cleared in three xylene baths before being mounted with Permount media.

Statistics

The significance of difference between two variables was assessed by the Student's t test. The difference was considered significant if the p value was <0.05. Data from all experiments are expressed as mean±standard error mean (SEM). All statistical calculations were performed using GraphPad Prism and Microsoft Excel.

Results

Selection of Phages Binding to Breast Cancer Cells that have Undergone EMT

MCF-7 (epithelial-luminal subtype) breast cancer cells were transformed into mesenchymal phenotype by long-term treatment with TGFβ (1 ng/mL for 30 days). FIG. 1 shows the change of MCF-7 breast cancer cells change in morphology upon TGFβ treatment.

Figure 2:
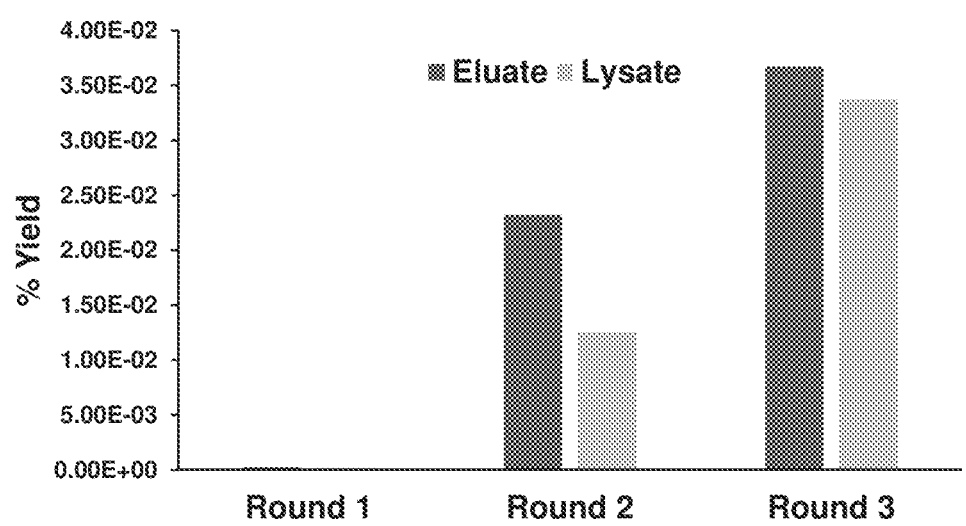
FIG. 2 depicts specific enrichment of eluate and lysate MCF-7-TGFβ cell-binding phage isolated from PhD CX7C library during three rounds of selection.
Figure 3A:
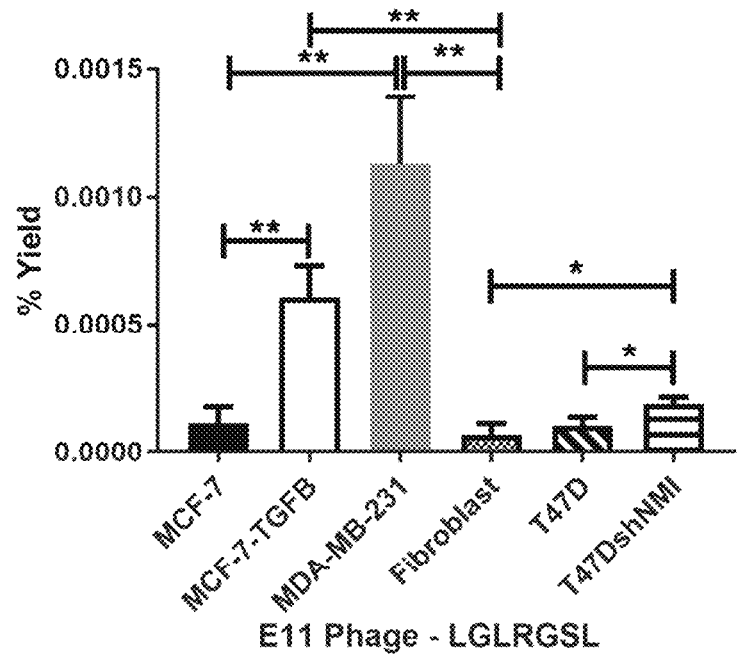
FIG. 3A-FIG. 3G presents affinity elected eluate and lysate phage displaying higher binding to MCF-7-TGFβ, MDA-MB-231, and T47D-shNMI cells as compared to breast Fibroblast, T47D and MCF-7 cells in phage capture assay.
Figure 3B:
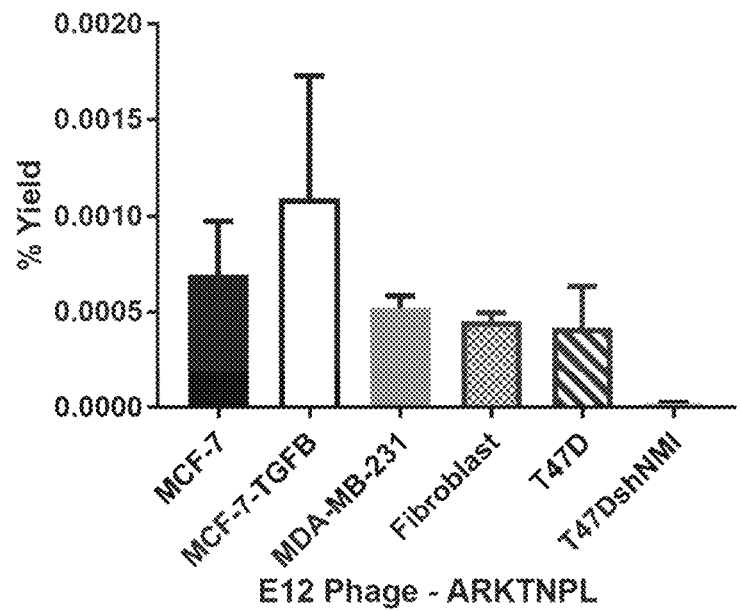
Figure 3C:
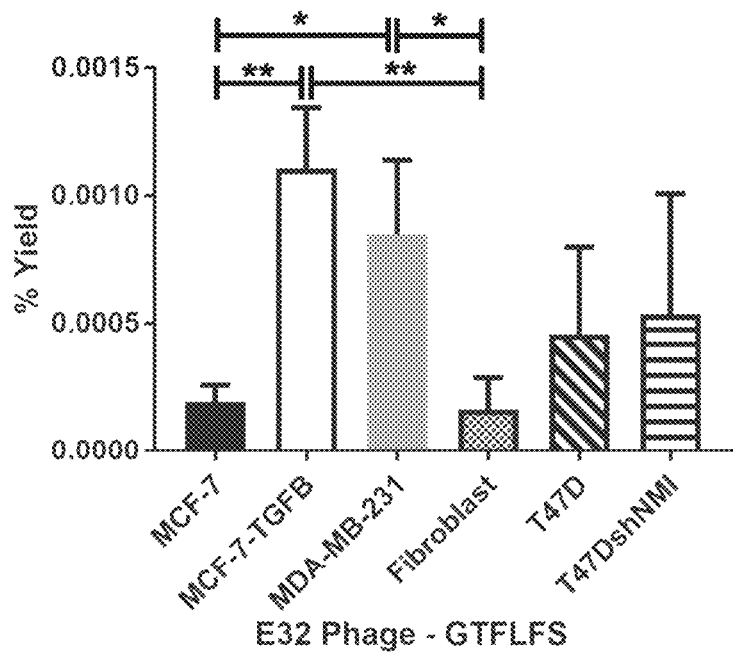
Figure 3D:
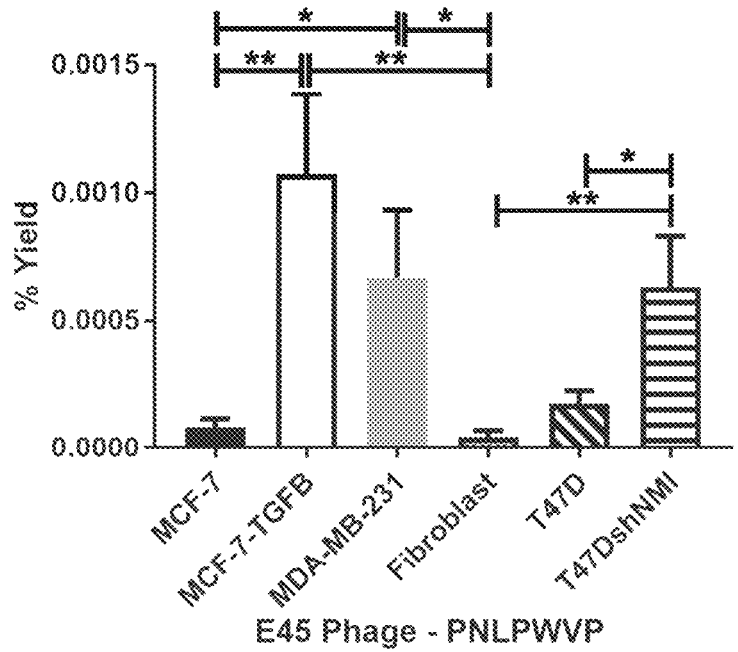
Figure 3E:
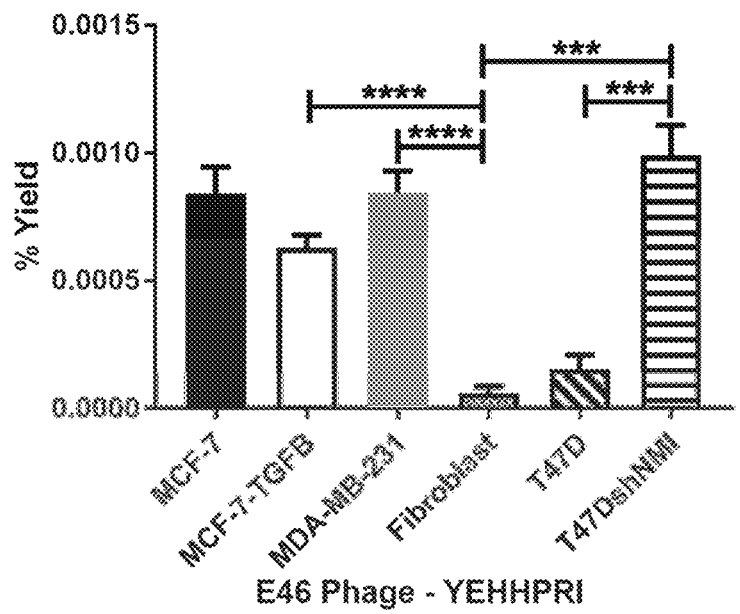
Figure 3F:
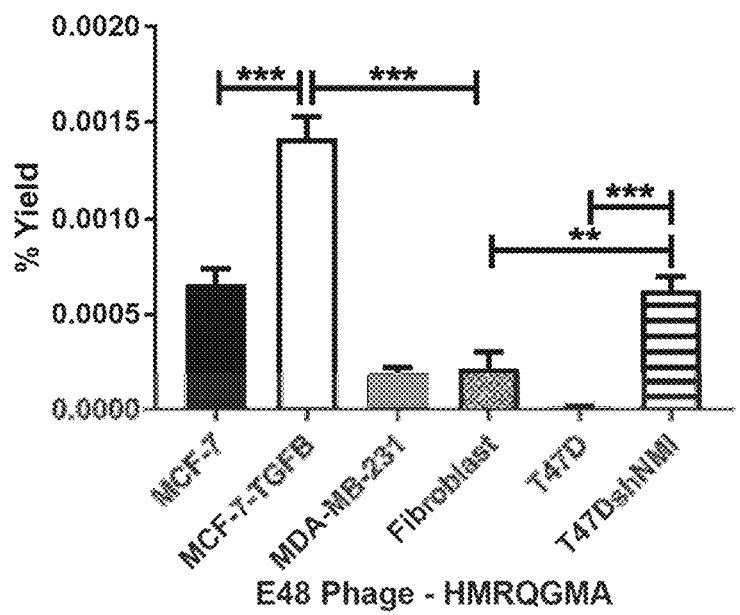
Figure 3G:
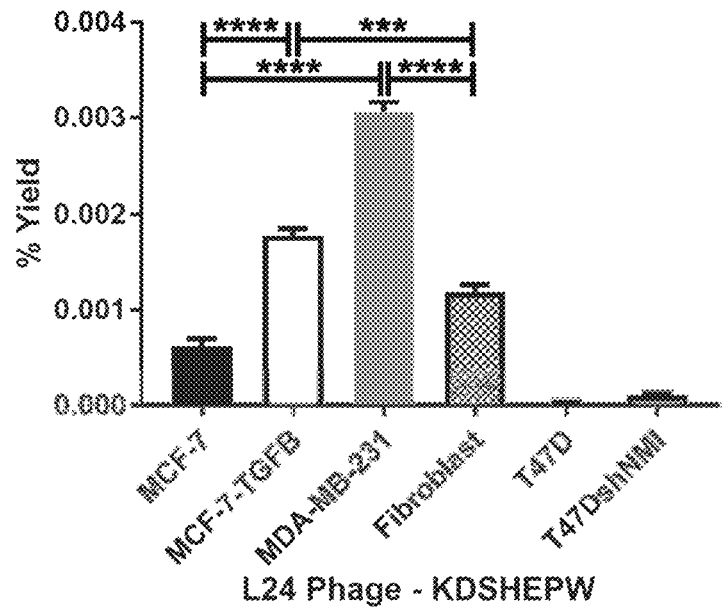
Figure 3H:
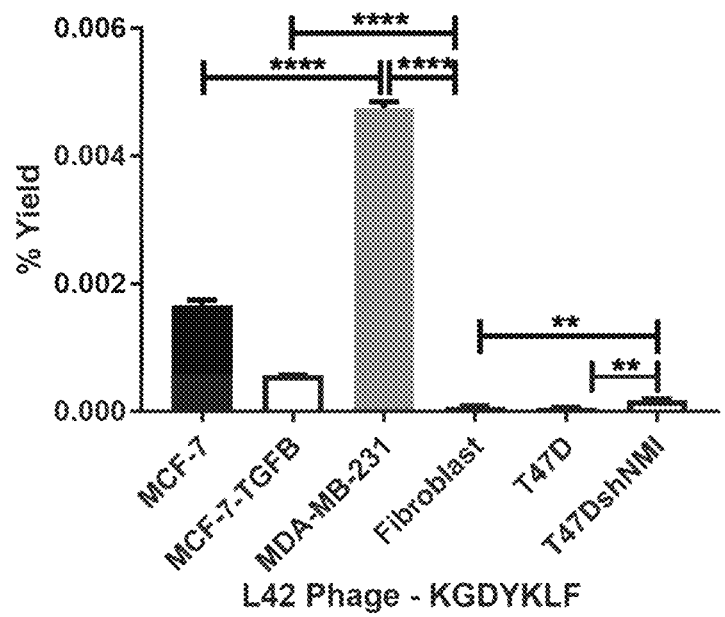
FIG. 3H is L42 phage KGDYKLF (SEQ ID NO: 8).
Figure 4A:
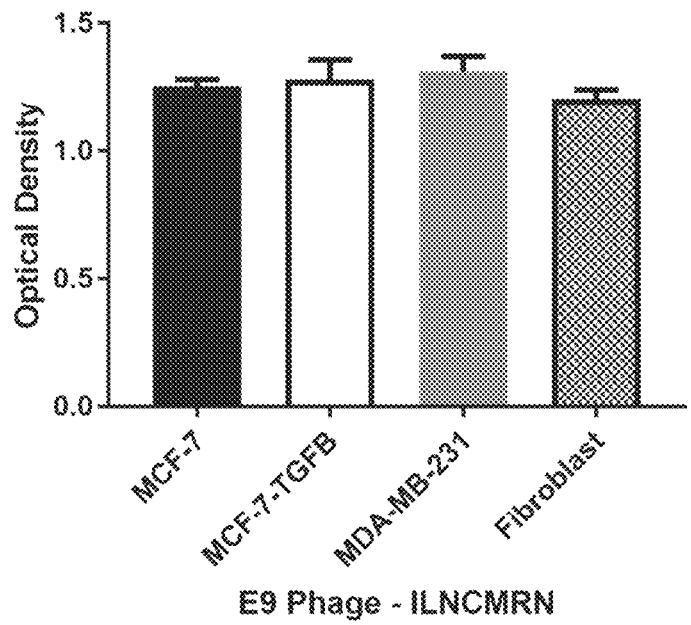
FIG. 4A-4G presents affinity elected eluate and lysate phage displaying higher binding to MCF-7-TGFβ, MDA-MB-231, T47D-shNMI cells as compared to breast Fibroblast, T47D and MCF-7 cells in phage based-ELISA.
Figure 4B:
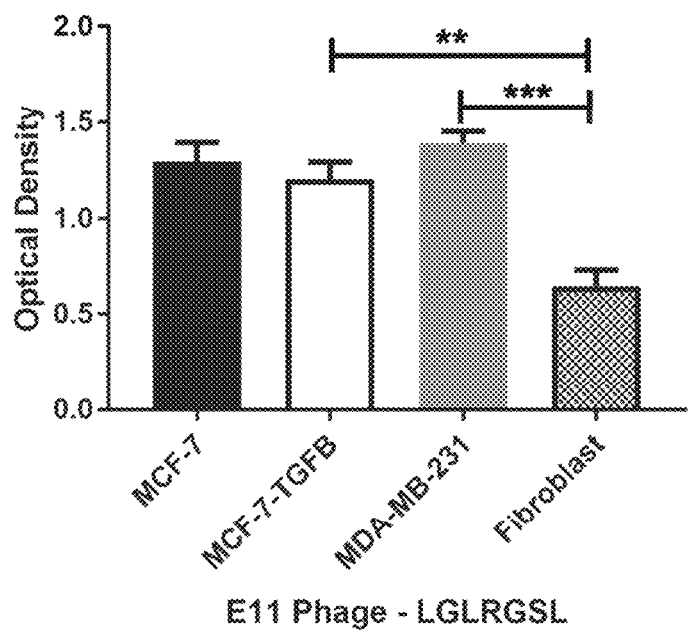
Figure 4C:
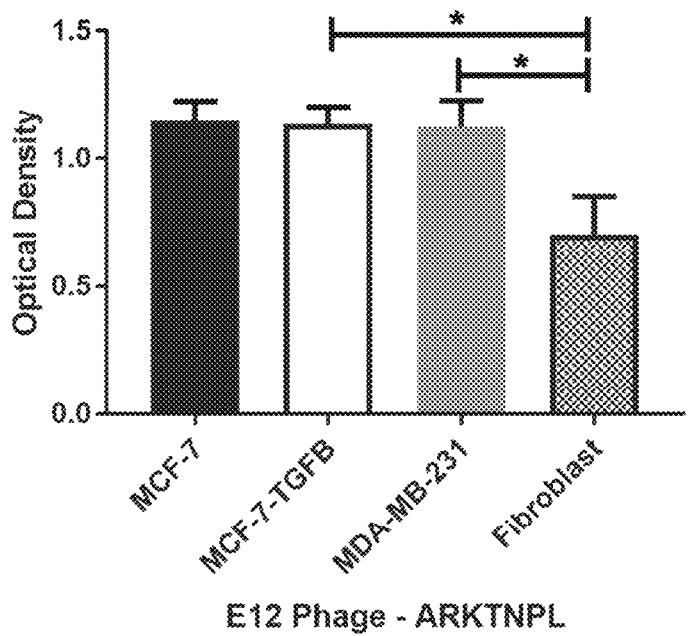
Figure 4D:
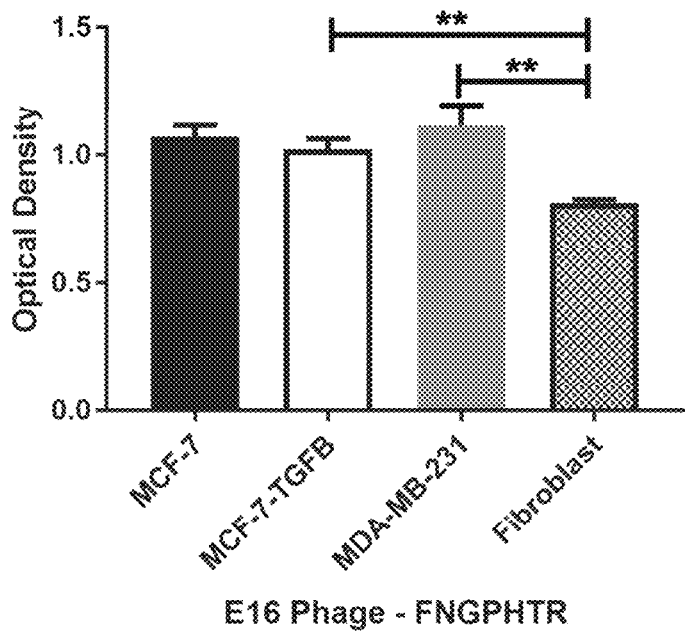
Figure 4E:
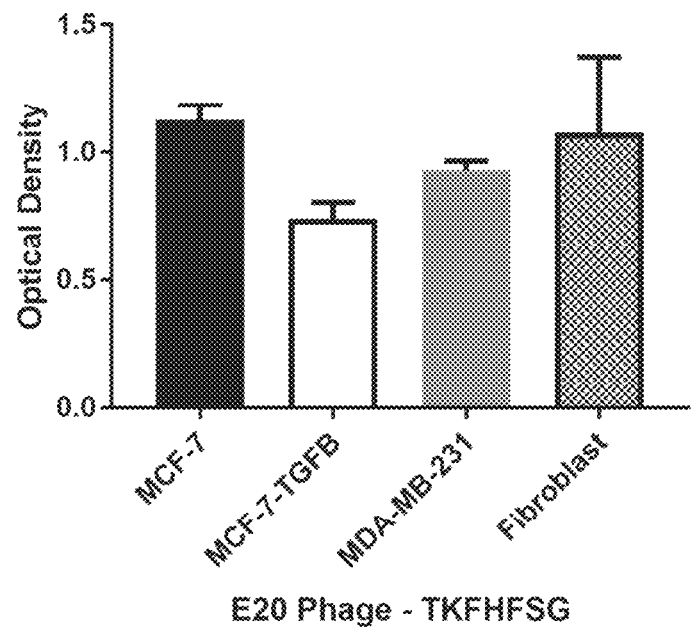
Figure 4F:
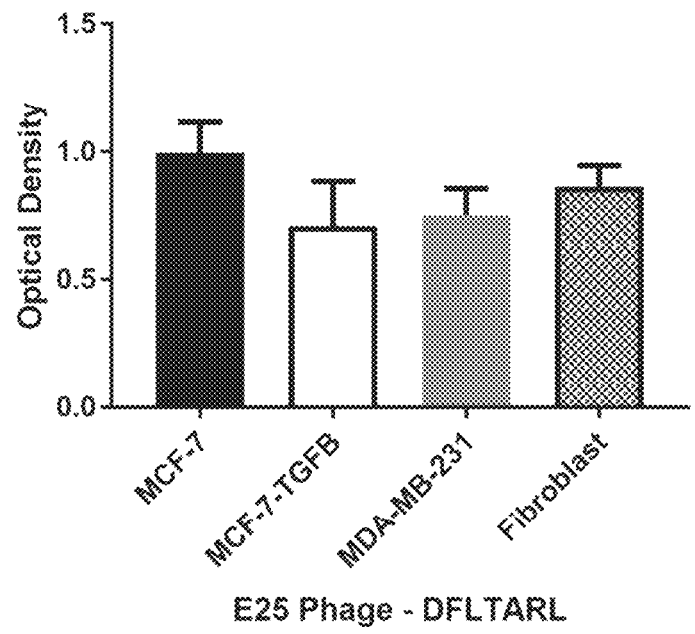
Figure 4G:
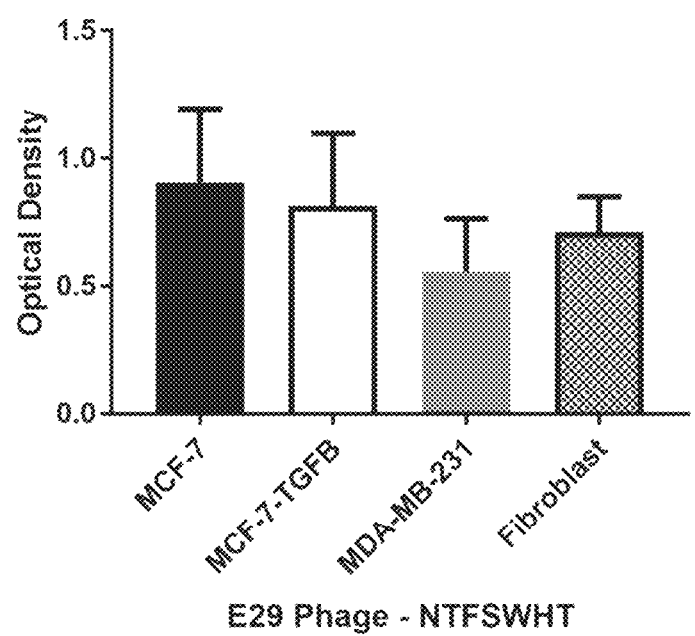

CX7C PhD phage library (NEB) was used to find phage clones that bind with high specificity and selectivity to MCF-7/TGFβ cells. Extensive depletion of the phage library against plastic, breast fibroblasts before enrichment of phage that interact with MCF-7-TGFβ breast cancer cells was employed for a robust selection of phage clones specific for cancer cells. This negative selection step was also performed after each round of panning on the MCF-7-TGFβ cells. Three such rounds of biopanning were performed on and in every round. Phage library and sub-library was depleted against breast fibroblasts to preferentially select for phages that did not bind to normal fibroblasts. Phage particles associated with cells were eluted sequentially with acid and detergents. The ratio of output to input phage increased from one round to another indicating successful enrichment for phage clones that bind to the target MCF-7-TGFβ cells (FIG. 2). The titers of recovered phages from each round were evaluated by blue plaque-forming assay on an agar plate. The phage enrichment rate was calculated as yield (%) which is as output number/input number×100. After the third round of selection, 100 phage clones were randomly picked after titering of the eluate, and lysate fractions. Their DNA was isolated, sequenced and translated to reveal the structures of the pIII fusion peptides. In total, 21 phage clones were isolated and classified based on their consensus linear peptide motifs (FIG. 8, Table I).

Selectivity of Phages Towards Mesenchymal-Like Breast Cancer Cells

Figure 5:
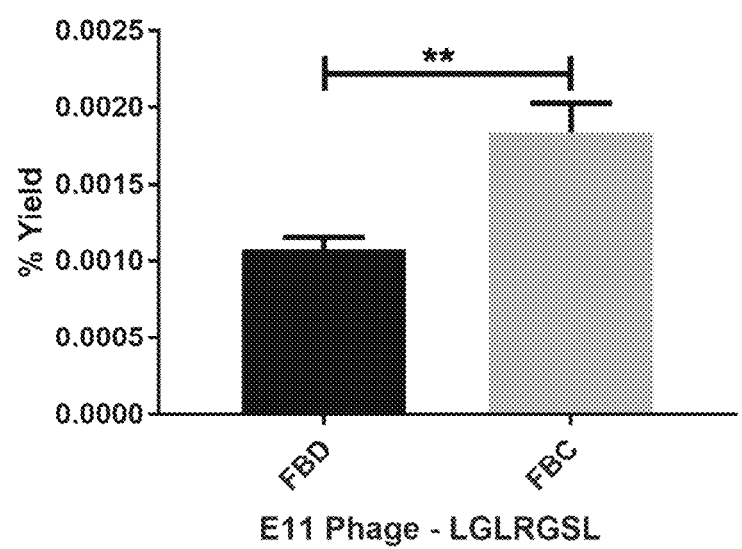
FIG. 5 shows that LGLRGSL (SEQ ID NO: 1) (E11) was also highly reactive to activated fibroblasts. FBD denotes fibroblasts in normal fibroblast media and FBC denotes fibroblasts in MDA-MB-231 breast cancer cell conditioned media. All data represent the mean±S.D. $*p<0.05$, $p\leq0.01$, $*p\leq0.001$, $****p\leq0.0001$.
Figure 6A:
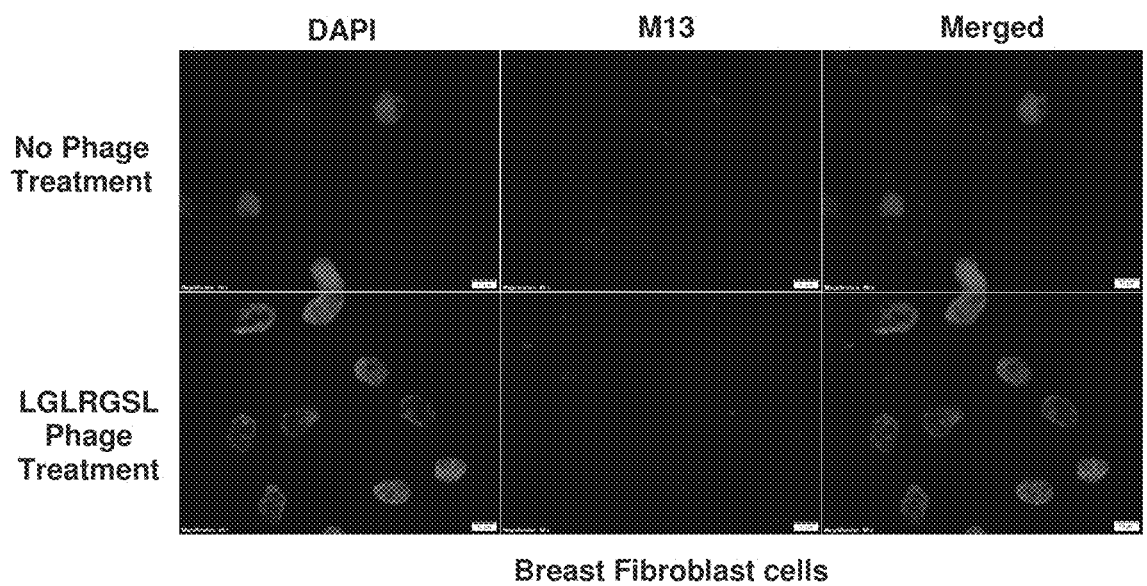
FIG. 6A provides study in breast fibroblast cells. The upper panel is where the cells were not exposed to phage. The lower panel is where the cells were exposed to phage LGLRGSL (SEQ ID NO: 1) (stained with DAPI and Alexa 488).
Figure 6B:
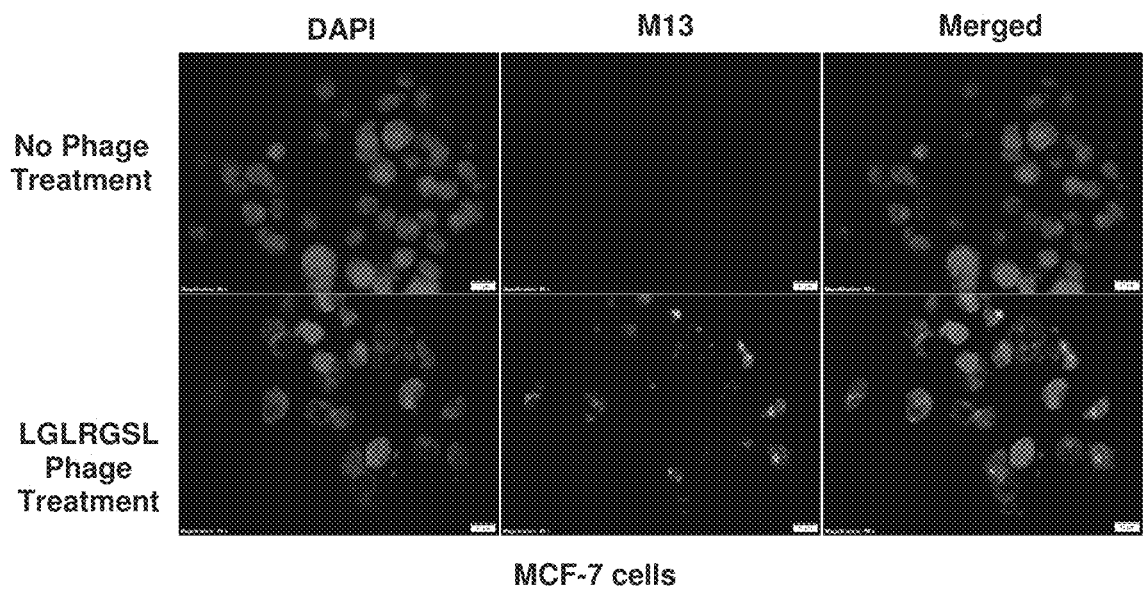
FIG. 6B provides study in MCF-7 cells. The upper panel is where the cells were not exposed to phage. The lower panel is where the cells were exposed to phage LGLRGSL (SEQ ID NO: 1).
Figure 6C:
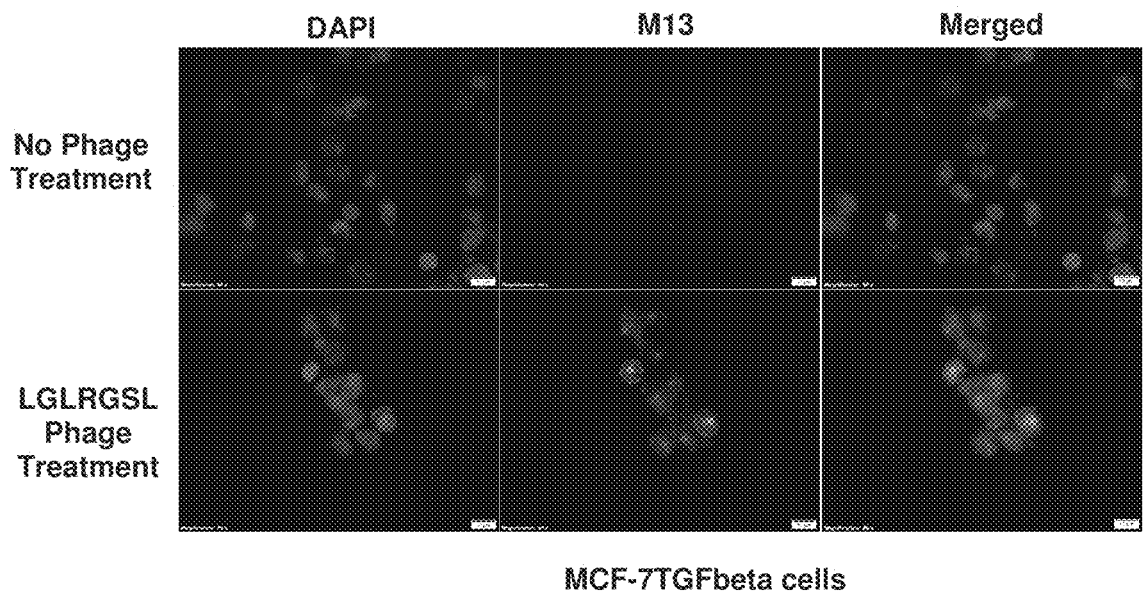
FIG. 6C provides study in MCF-7/TGFβ cells. The upper panel is where the cells were not exposed to phage. The lower panel is where the cells were exposed to phage LGLRGSL (SEQ ID NO: 1).
Figure 6D:
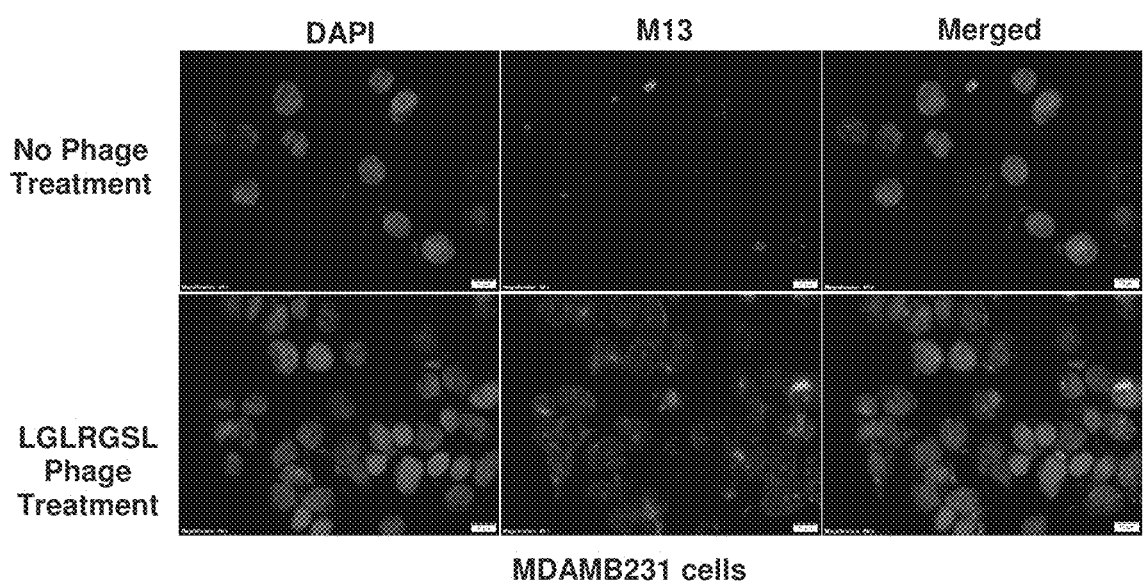
FIG. 6D provides study in MDA-MB-231. The upper panel is where the cells were not exposed to phage. The lower panel is where the cells were exposed to phage LGLRGSL (SEQ ID NO: 1).

Phage clones obtained by screening of the CX7C phage library against MCF-7/TGFβ cancer cells were tested for their selective binding towards the target MCF-7/TGFβ, MDA-MB-231, and T47D-shNMI cells and not to breast fibroblasts or epithelial subtype breast cancer cells MCF-7 and T47D in phage capture assay (FIGS. 3A-3I and FIGS. 4A-4G) and phage based ELISA (FIG. 5). In FIG. 6, FBD denotes fibroblasts in normal fibroblast media and FBC denotes fibroblasts in MDA-MB-231 breast cancer cell conditioned media. All data represent the mean±S.D. *p<0.05, p≤0.01, *p≤0.001, ****p≤0.0001.

The cells lines MCF-7/TGFβ, MDA-MB-231, and T47D-NMI exhibit mesenchymal phenotype or markers of EMT and are aggressive, and structurally similar to fibroblasts and also express markers of EMT and thus, are representation of EMT in breast cancer cells. The MDA-MB-231 breast cancer cell line exhibits mesenchymal phenotype and are denoted as EMT phenotype [33]. T47D-NMI is an epithelial breast cancer cell line and was transitioned to EMT by silencing a gene, N-myc and STAT interactor [34].

In these assays, some phages demonstrated high selectivity towards EMT cells, while other phages showed selectivity for epithelial breast cancer cells as well as breast fibroblasts. Phages were considered selective if their relative binding to EMT phenotypic cells (MCF-7/TGFβ, MDA-MB-231 and T47D-shNMI) were at least five times higher than those of epithelial breast cancer cells (MCF-7 and T47D) and breast fibroblasts. KGDYKLF (SEQ ID NO: 8) (L42), phage selected from lysate fraction, showed a high specificity towards MDA-MB-231 cells but was not so selective towards MCF-7/TGFβ, MCF-7 and breast fibroblasts. Phages selected from eluate fraction {LGLRGSL (SEQ ID NO: 1) (E11), GTFLFS (SEQ ID NO: 3) (E32) and PNLPWVP (SEQ ID NO: 4) (E45)} were very selective for EMT phenotypic cells (MCF-7/TGFβ, MDA-MB-231 and T47D-shNMI) and showed more than 10 times binding as compared to its binding to breast fibroblasts and epithelial breast cancer cells (MCF-7 and T47D) in phage capture assay (FIG. 3A-3I). Phage E11 was confirmatory for its selectivity towards EMT cells in phage-based ELISA (FIG. 5) and thus was chosen for further characterization.

To determine if E11 could recognize EMT phenotype in other cell types of tumor microenvironment, E11 was screened against activated fibroblasts (fibroblasts converted to CAF's by treatment with cancer-conditioned media). E11 demonstrated higher binding (twice as much) to activated-fibroblasts than normal fibroblasts (FIG. 5).

Example 4: Validation of Phage Peptide Binding to EMT Target Cells In Vitro Using Immunofluoresence Analysis To further confirm the specificity of LGLRGSL (SEQ ID NO: 1) (E11) towards breast cancer cells with an EMT phenotype, immunofluorescence microscopy of intact cells (MCF-7/TGF β and MDA-MB-231), and control MCF-7 breast cancer cells and breast fibroblasts (Hs578T) were used. All cells were treated with the phage ($10^8$ pfu) at RT for 1 hr, and subsequently incubated with primary anti-pIII antibody and then stained with secondary anti-mouse Alexa fluor 488 secondary antibody. LGLRGSL (SEQ ID NO: 1) (E11) showed almost no binding to breast fibroblasts (FIG. 6A), some staining to MCF-7 cells (FIG. 6B), while abundant binding to EMT cells, MCF-7/TGFβ (FIG. 6C) and MDA-MB-231 (FIG. 6D) as shown by green fluorescent phage staining. No background antibody was observed as shown in the respective controls of cells treated with just primary and secondary antibodies.

Example 5: Validation of Phage Peptide Binding to Human Breast Cancer Ex Vivo

Figure 7A:
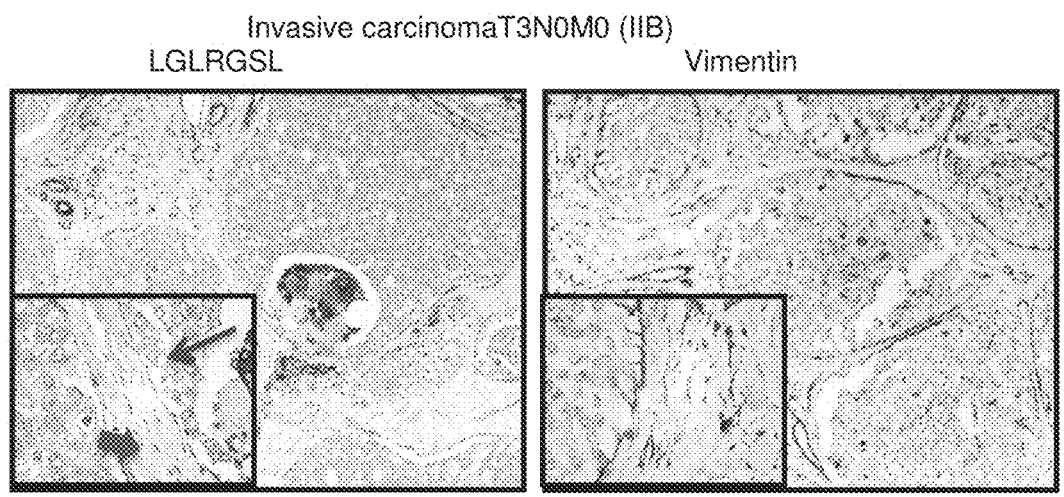
FIG. 7A-7E presents results of ex vivo phage binding to a human breast cancer tissue microarray. Tissue microarray of invasive ductal carcinoma and adjacent normal tissues were incubated with 1010 pfu of LGLRGSL phage (SEQ ID NO: 1) or Vimentin antibody and then subsequently with M13-pIII antibody for phage and secondary peroxidase antibody for phage and Vimentin, imaged with a digital light microscope. Strong brown staining of the phage and Vimentin was observed in invasive ductal carcinoma sections.
Figure 7B:
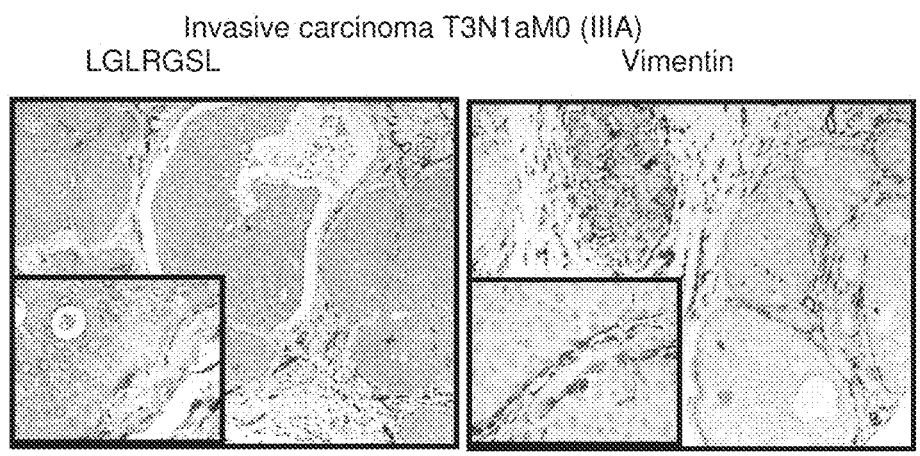
Figure 7C:
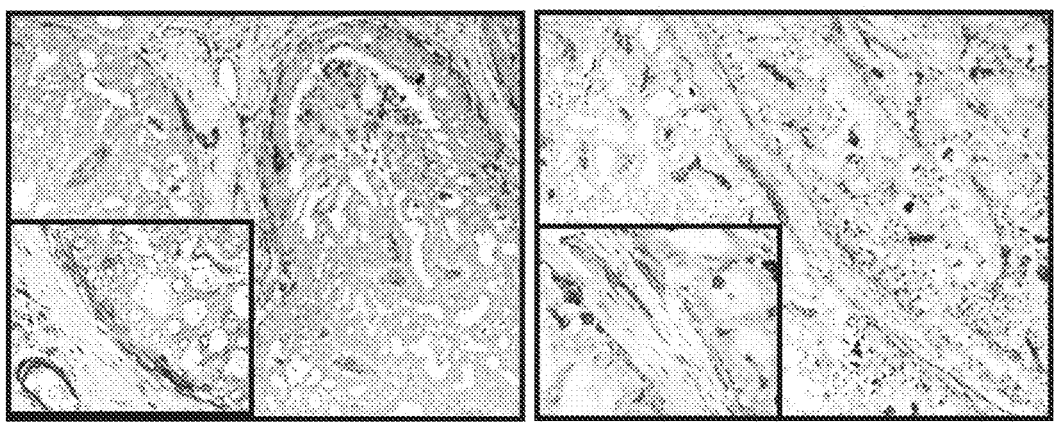
Figure 7D:
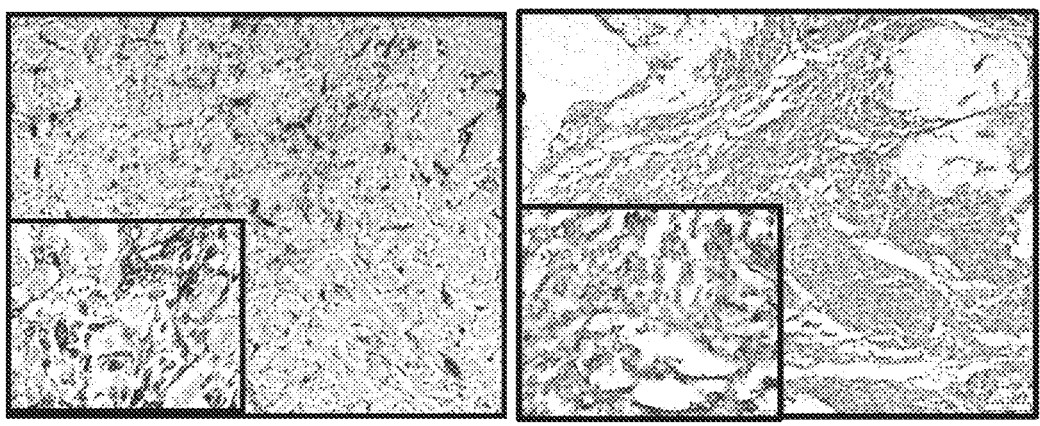
Figure 7E:
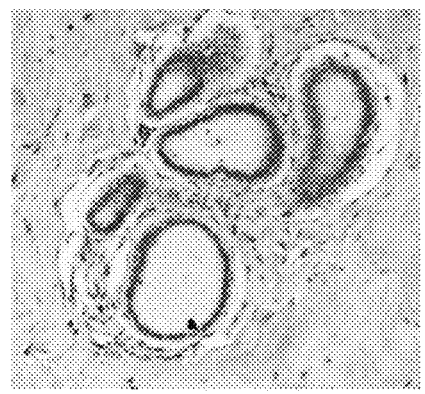

The clinical relevance of LGLRGSL (SEQ ID NO: 1) (E11) was assessed for utility to prospectively identify human invasive ductal carcinoma (IDC) breast tumors with a propensity to metastasize as metastatic cells undergo EMT before metastasizing [35]. Immunostaining for phage in human breast cancer tissue indicated phage has substantial staining for invasive ductal breast cancer carcinoma (FIG. 7A, FIG. 7B and FIG. 7C, left) and its staining intensity increased in tumors invading into adjacent lymph nodes (FIG. 7D). Furthermore, no binding in normal breast tissues was observed (FIG. 7E). We observed that vimentin, a mesenchymal marker, within the same TMA (FIG. 7A, FIG. 7B and FIG. 7C, right) demonstrated a different staining pattern than the LGLRGSL (SEQ ID NO: 1) (E11) phage (FIG. 4, upper and lower). Vimentin showed stromal staining; however, phage was immunoreactive to the tumor cells with robust staining around the invasive or leading edge of the tumor-stromal interaction.

REFERENCES

[1] A. Jemal, R. Siegel, E. Ward, Y. Hao, J. Xu, and M. J. Thun, Cancer statistics, 2009. CA: a cancer journal for clinicians 59 (2009) 225-49.

[2] D. Weng, J. H. Penzner, B. Song, S. Koido, S. K. Calderwood, and J. Gong, Metastasis is an early event in mouse mammary carcinomas and is associated with cells bearing stem cell markers. Breast Cancer Research: BCR 14 (2012) R18-R18.

[3] J. H. Tsai, J. L. Donaher, D. A. Murphy, S. Chau, and J. Yang, Spatiotemporal regulation of epithelial-mesenchymal transition is essential for squamous cell carcinoma metastasis. Cancer cell 22 (2012) 725-36.

[4] M. E. Menezes, D. J. Devine, L. A. Shevde, and R. S. Samant, Dickkopf1: a tumor suppressor or metastasis promoter? International journal of cancer 130 (2012) 1477-83.

[5] D. F. Quail, and J. A. Joyce, Microenvironmental regulation of tumor progression and metastasis. Nature medicine 19 (2013) 1423-37.

[6] Y. Wang, and B. P. Zhou, Epithelial-mesenchymal transition in breast cancer progression and metastasis. Chinese journal of cancer 30 (2011) 603-11.

[7] A. J. Trimboli, K. Fukino, A. de Bruin, G. Wei, L. Shen, S. M. Tanner, N. Creasap, T. J. Rosol, M. L. Robinson, C. Eng, M. C. Ostrowski, and G. Leone, Direct evidence for epithelial-mesenchymal transitions in breast cancer. Cancer research 68 (2008) 937-45.

[8] L. G. Harris, R. S. Samant, and L. A. Shevde, Hedgehog signaling: networking to nurture a promalignant tumor microenvironment. Molecular cancer research: MCR 9 (2011) 1165-74.

[9] M. H. Barcellos-Hoff, and R. J. Akhurst, Transforming growth factor-beta in breast cancer: too much, too late. Breast Cancer Res 11 (2009) 202.

[10] J. Gotzmann, A. N. Fischer, M. Zojer, M. Mikula, V. Proell, H. Huber, M. Jechlinger, T. Waerner, A. Weith, H. Beug, and W. Mikulits, A crucial function of PDGF in TGF-beta-mediated cancer progression of hepatocytes. Oncogene 25 (2006) 3170-85.

[11] P. J. Miettinen, R. Ebner, A. R. Lopez, and R. Derynck, TGF-beta induced transdifferentiation of mammary epithelial cells to mesenchymal cells: involvement of type I receptors. The Journal of cell biology 127 (1994) 2021-36.

[12] H. Li, X. Fan, and J. Houghton, Tumor microenvironment: the role of the tumor stroma in cancer. Journal of cellular biochemistry 101 (2007) 805-15.

[13] A. Mitra, M. E. Menezes, L. A. Shevde, and R. S. Samant, DNAJB6 induces degradation of beta-catenin and causes partial reversal of mesenchymal phenotype. The Journal of biological chemistry 285 (2010) 24686-94.

[14] S. E. Moody, D. Perez, T. C. Pan, C. J. Sarkisian, C. P. Portocarrero, C. J. Sterner, K. L. Notorfrancesco, R. D. Cardiff, and L. A. Chodosh, The transcriptional repressor Snail promotes mammary tumor recurrence. Cancer cell 8 (2005) 197-209.

[15] K. A. Morrow, S. Das, B. J. Metge, K. Ye, M. S. Mulekar, J. A. Tucker, R. S. Samant, and L. A. Shevde, Loss of tumor suppressor Merlin in advanced breast cancer is due to post-translational regulation. The Journal of biological chemistry 286 (2011) 40376-85.

[16] M. Zeisberg, and E. G. Neilson, Biomarkers for epithelial-mesenchymal transitions. The Journal of clinical investigation 119 (2009) 1429-37.

[17] W. W. Franke, E. Schmid, M. Osborn, and K. Weber, Different intermediate-sized filaments distinguished by immunofluorescence microscopy. Proceedings of the National Academy of Sciences of the United States of America 75 (1978) 5034-8.

[18] K. Dellagi, W. Vainchenker, G. Vinci, D. Paulin, and J. C. Brouet, Alteration of vimentin intermediate filament expression during differentiation of human hemopoietic cells. The EMBO Journal 2 (1983) 1509-1514.

[19] G. P. Smith, and V. A. Petrenko, Phage Display. Chemical Reviews 97 (1997) 391-410.

[20] V. A. Petrenko, G. P. Smith, X. Gong, and T. Quinn, A library of organic landscapes on filamentous phage. Protein engineering 9 (1996) 797-801.

[21] K. A. Kelly, and D. A. Jones, Isolation of a colon tumor specific binding peptide using phage display selection. Neoplasia (New York, N.Y.) 5 (2003) 437-44.

[22] J. R. Newton, K. A. Kelly, U. Mahmood, R. Weissleder, and S. L. Deutscher, In vivo selection of phage for the optical imaging of PC-3 human prostate carcinoma in mice. Neoplasia (New York, N.Y.) 8 (2006) 772-80.

[23] P. K. Jayanna, D. Bedi, P. Deinnocentes, R. C. Bird, and V. A. Petrenko, Landscape phage ligands for PC3 prostate carcinoma cells. Protein Engineering, Design and Selection 23 (2010) 423-430.

[24] K. A. Kelly, N. Bardeesy, R. Anbazhagan, S. Gurumurthy, J. Berger, H. Alencar, R. A. Depinho, U. Mahmood, and R. Weissleder, Targeted nanoparticles for imaging incipient pancreatic ductal adenocarcinoma. PLoS medicine 5 (2008) e85.

[25] G. S. Shukla, and D. N. Krag, Cancer cell-specific internalizing ligands from phage displayed β-lactamase-peptide fusion libraries. Protein Engineering, Design and Selection 23 (2010) 431-440.

[26] O. A. Fagbohun, D. Bedi, N. I. Grabchenko, P. A. Deinnocentes, R. C. Bird, and V. A. Petrenko, Landscape phages and their fusion proteins targeted to breast cancer cells. Protein engineering, design & selection: PEDS 25 (2012) 271-83.

[27] T. Wang, G. G. D'Souza, D. Bedi, O. A. Fagbohun, L. P. Potturi, B. Papahadjopoulos-Sternberg, V. A. Petrenko, and V. P. Torchilin, Enhanced binding and killing of target tumor cells by drug-loaded liposomes modified with tumor-specific phage fusion coat protein. Nanomedicine (London, England) 5 (2010) 563-74.

[28] D. Bedi, T. Musacchio, O. A. Fagbohun, J. W. Gillespie, P. Deinnocentes, R. C. Bird, L. Bookbinder, V. P. Torchilin, and V. A. Petrenko, Delivery of siRNA into breast cancer cells via phage fusion protein-targeted liposomes. Nanomedicine: nanotechnology, biology, and medicine 7 (2011) 315-23.

[29] P. K. Jayanna, D. Bedi, J. W. Gillespie, P. Delnnocentes, T. Wang, V. P. Torchilin, R. C. Bird, and V. A. Petrenko, Landscape Phage Fusion Protein-mediated Targeting of Nanomedicines Enhances their Prostate Tumor Cell Association and Cytotoxic Efficiency. Nanomedicine: nanotechnology, biology, and medicine 6 (2010) 538-546.

[30] U. B. Rasmussen, V. Schreiber, H. Schultz, F. Mischler, and K. Schughart, Tumor cell-targeting by phage-displayed peptides. Cancer gene therapy 9 (2002) 606-12.

[31] T. Teesalu, K. N. Sugahara, and E. Ruoslahti, Mapping of vascular ZIP codes by phage display. Methods in enzymology 503 (2012) 35-56.

[32] X. B. Li, H. J. Schluesener, and S. Q. Xu, Molecular addresses of tumors: selection by in vivo phage display. Archivum immunologiae et therapiae experimentalis 54 (2006) 177-81.

[33] N. C. D'Amato, J. H. Ostrander, M. L. Bowie, C. Sistrunk, A. Borowsky, R. D. Cardiff, K. Bell, L. J. Young, K. Simin, R. E. Bachelder, J. Delrow, A. Dawson, L. D. Yee, K. Mrozek, T. M. Clay, T. Osada, and V. L. Seewaldt, Evidence for phenotypic plasticity in aggressive triple-negative breast cancer: human biology is recapitulated by a novel model system. PloS one 7 (2012) e45684.

[34] D. J. Devine, J. W. Rostas, B. J. Metge, S. Das, M. S. Mulekar, J. A. Tucker, W. E. Grizzle, D. J. Buchsbaum, L. A. Shevde, and R. S. Samant, Loss of N-Myc interactor promotes epithelial-mesenchymal-transition by activation of TGF-β/SMAD signaling. Oncogene 33 (2014) 2620-2628.

[35] S. Heerboth, G. Housman, M. Leary, M. Longacre, S. Byler, K. Lapinska, A. Willbanks, and S. Sarkar, EMT and tumor metastasis. Clinical and Translational Medicine 4 (2015) 6.

[36] P. Schedin, and V. Borges, Breaking down barriers: the importance of the stromal microenvironment in acquiring invasiveness in young women's breast cancer. Breast Cancer Res 11 (2009) 102.

[37] R. Kalluri, and M. Zeisberg, Fibroblasts in cancer. Nature reviews. Cancer 6 (2006) 392-401.

[38] M. L. Tejada, L. Yu, J. Dong, K. Jung, G. Meng, F. V. Peale, G. D. Frantz, L. Hall, X. Liang, H. P. Gerber, and N. Ferrara, Tumor-driven paracrine platelet-derived growth factor receptor alpha signaling is a key determinant of stromal cell recruitment in a model of human lung carcinoma. Clinical cancer research: an official journal of the American Association for Cancer Research 12 (2006) 2676-88.

[39] U. E. Martinez-Outschoorn, C. Trimmer, Z. Lin, D. Whitaker-Menezes, B. Chiavarina, J. Zhou, C. Wang, S. Pavlides, M. P. Martinez-Cantarin, F. Capozza, A. K. Witkiewicz, N. Flomenberg, A. Howell, R. G. Pestell, J. Caro, M. P. Lisanti, and F. Sotgia, Autophagy in cancer associated fibroblasts promotes tumor cell survival: Role of hypoxia, HIF1 induction and NFkappaB activation in the tumor stromal microenvironment. Cell cycle (Georgetown, Tex.) 9 (2010) 3515-33.

[40] E. Giannoni, F. Bianchini, L. Masieri, S. Semi, E. Tone, L. Calorini, and P. Chiarugi, Reciprocal activation of prostate cancer cells and cancer-associated fibroblasts stimulates epithelial-mesenchymal transition and cancer stemness. Cancer research 70 (2010) 6945-56.

What is claimed is:

1. An isolated peptide consisting of amino acid sequence of LGLRGSL (SEQ ID NO: 1), or GTFLFS (SEQ ID NO: 3) or PNLPWVP (SEQ ID NO: 4) complexed with a detectable label.

2. The peptide of claim 1 wherein the peptide is complexed with a radio-isotope, biotin, digoxygenin, methyl, fluorescence or a chemiluminescent.

3. An expression vector comprising a nucleic acid sequence encoding the amino acid sequence consisting of LGLRGSL (SEQ ID NO:1), or GTLFLFS (SEQ ID NO: 3) or PNLPWVP (SEQ ID NO: 4) operably linked to a promoter.

4. A method of determining whether a subject has or is at risk for metastatic breast cancer, the method comprising:
providing a peptide complex, wherein the peptide complex specifically binds to EMT phenotypic breast cancer cells and does not specifically bind to non-cancer cells,
delivering the peptide complex to a subject; and
detecting the peptide complex in a subject, wherein the presence of the peptide complex indicates that the subject has or is at risk for a metastatic breast cancer;
wherein the peptide has the sequence selected from the group consisting of SEQ ID NOs: 1-7, 9-14, 16-24 and 25.

5. A method of determining whether a subject has or is at risk for metastatic breast cancer, the method comprising:
providing a biological sample from the subject;
contacting the biological sample with the peptide of claim 2, wherein the peptide specifically binds to EMT phenotypic breast cancer cells and does not specifically bind to non-cancer cells; and
detecting the binding of the peptide to EMT phenotypic breast cancer cells in the biological sample, thereby determining the biological sample contains EMT phenotypic breast cancer cells,
wherein the presence of EMT phenotypic breast cancer cells in the biological sample indicates that the subject has or is at risk for a metastatic breast cancer.

6. The method of claim 4, wherein the biological sample is a tissue biopsy, a lymph node biopsy tumor, serum, blood, or plasma sample.

* * * * *

SEQUENCE LISTING

<160> NUMBER OF SEQ ID NOS: 27

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Gly Leu Arg Gly Ser Leu
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Arg Lys Thr Asn Pro Leu
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Thr Phe Leu Phe Ser
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro Asn Leu Pro Trp Val Pro
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Glu His His Pro Arg Ile
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic

```
                       peptide

<400> SEQUENCE: 6

His Met Arg Gln Gly Met Ala
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Asp Ser His Glu Pro Trp
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Gly Asp Tyr Lys Leu Phe
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Pro Val Leu Leu Gly Glu Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Leu Asn Cys Met Arg Asn
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Asn Gly Pro His Thr Arg
1               5

<210> SEQ ID NO 12
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Lys Phe His Phe Ser Gly
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Phe Leu Thr Ala Arg Leu
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asn Thr Phe Ser Trp His Thr
1               5

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccctcatagt tagcgtaacg                                                   20

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Thr Leu Arg Thr Pro Tyr
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

His His Asp Asn Val Ala Met
```

```
<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr His Ser Ser Trp Gly Met
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Met Trp Glu Ser Val Pro
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Glu Gly His Met Gly Val
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Leu Ala Thr Gly Gly Met
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Pro Tyr Glu Pro Arg Ala Thr
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 23

Ser Ile Leu Ser Lys Asn His
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Arg Ser Gly Met His Ser
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

His Trp Pro Ala Lys His Ile
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Leu Gly Leu Arg Gly Ser Leu Cys
1               5

<210> SEQ ID NO 27
<211> LENGTH: 573
<212> TYPE: PRT
<213> ORGANISM: Homo sapiens

<400> SEQUENCE: 27

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
```

```
            115                 120                 125
Glu Lys Ile Ser Lys Gly Ala Asn Pro Val Glu Ile Arg Arg Gly Val
            130                 135                 140
Asn Leu Ala Val Asp Ala Val Ile Ala Glu Leu Lys Lys Gln Ser Lys
145                 150                 155                 160
Pro Val Thr Thr Pro Glu Glu Ile Ala Gln Val Ala Thr Ile Ser Ala
                165                 170                 175
Asn Gly Asp Lys Glu Ile Gly Asn Ile Ile Ser Asp Ala Asn Lys Lys
            180                 185                 190
Val Gly Arg Lys Gly Val Ile Thr Val Lys Asp Gly Lys Thr Leu Asn
            195                 200                 205
Asp Glu Leu Glu Ile Ile Glu Gly Met Lys Phe Asp Arg Gly Tyr Ile
            210                 215                 220
Ser Pro Tyr Phe Ile Asn Thr Ser Lys Gly Gln Lys Cys Glu Phe Gln
225                 230                 235                 240
Asp Ala Tyr Val Leu Leu Ser Glu Lys Lys Ile Ser Ser Ile Gln Ser
                245                 250                 255
Ile Val Pro Ala Leu Glu Ile Ala Asn Ala His Arg Lys Pro Leu Val
            260                 265                 270
Ile Ile Ala Glu Asp Val Asp Gly Glu Ala Leu Ser Thr Leu Val Leu
            275                 280                 285
Asn Arg Leu Lys Val Gly Leu Gln Val Val Ala Val Lys Ala Pro Gly
290                 295                 300
Phe Gly Asp Asn Arg Lys Asn Gln Leu Lys Asp Met Ala Ile Ala Thr
305                 310                 315                 320
Gly Gly Ala Val Phe Gly Glu Glu Gly Leu Thr Leu Asn Leu Glu Asp
                325                 330                 335
Val Gln Pro His Asp Leu Gly Lys Val Gly Glu Val Ile Val Thr Lys
            340                 345                 350
Asp Asp Ala Met Leu Leu Lys Gly Lys Gly Asp Lys Ala Gln Ile Glu
            355                 360                 365
Lys Arg Ile Gln Glu Ile Ile Glu Gln Leu Asp Val Thr Thr Ser Glu
            370                 375                 380
Tyr Glu Lys Glu Lys Leu Asn Glu Arg Leu Ala Lys Leu Ser Asp Gly
385                 390                 395                 400
Val Ala Val Leu Lys Val Gly Gly Thr Ser Asp Val Glu Val Asn Glu
                405                 410                 415
Lys Lys Asp Arg Val Thr Asp Ala Leu Asn Ala Thr Arg Ala Ala Val
            420                 425                 430
Glu Glu Gly Ile Val Leu Gly Gly Gly Cys Ala Leu Leu Arg Cys Ile
            435                 440                 445
Pro Ala Leu Asp Ser Leu Thr Pro Ala Asn Glu Asp Gln Lys Ile Gly
450                 455                 460
Ile Glu Ile Ile Lys Arg Thr Leu Lys Ile Pro Ala Met Thr Ile Ala
465                 470                 475                 480
Lys Asn Ala Gly Val Glu Gly Ser Leu Ile Val Glu Lys Ile Met Gln
                485                 490                 495
Ser Ser Ser Glu Val Gly Tyr Asp Ala Met Ala Gly Asp Phe Val Asn
            500                 505                 510
Met Val Glu Lys Gly Ile Ile Asp Pro Thr Lys Val Val Arg Thr Ala
            515                 520                 525
Leu Leu Asp Ala Ala Gly Val Ala Ser Leu Leu Thr Thr Ala Glu Val
            530                 535                 540
```

```
-continued

Val Val Thr Glu Ile Pro Lys Glu Glu Lys Asp Pro Gly Met Gly Ala
545                 550                 555                 560

Met Gly Gly Met Gly Gly Gly Met Gly Gly Gly Met Phe
                565             570
```